(12) United States Patent
Chen et al.

(10) Patent No.: US 11,359,089 B2
(45) Date of Patent: Jun. 14, 2022

(54) METHOD FOR PREPARING Y-BRANCHED HYDROPHILIC POLYMER CARBOXYLIC ACID DERIVATIVE

(71) Applicant: JenKem Technology Co., Ltd. (Beijing), Beijing (CN)

(72) Inventors: Xiaomeng Chen, Beijing (CN); Meina Lin, Beijing (CN); Rujun Zhang, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 108 days.

(21) Appl. No.: 16/588,620

(22) Filed: Sep. 30, 2019

(65) Prior Publication Data

US 2020/0024446 A1 Jan. 23, 2020

Related U.S. Application Data

(63) Continuation of application No. PCT/CN2018/077229, filed on Feb. 26, 2018.

(30) Foreign Application Priority Data

Mar. 30, 2017 (CN) .......................... 201710202947.4
Sep. 29, 2017 (CN) .......................... 201710915311.4

(51) Int. Cl.
*C08L 71/12* (2006.01)
*C08G 65/333* (2006.01)

(52) U.S. Cl.
CPC ...... *C08L 71/126* (2013.01); *C08G 65/33396* (2013.01); *C08L 2203/02* (2013.01)

(58) Field of Classification Search
CPC ............................................. C08G 65/33396
See application file for complete search history.

(56) References Cited

U.S. PATENT DOCUMENTS

2010/0221213 A1* 9/2010 Ji ........................ C08G 65/329
424/85.4

FOREIGN PATENT DOCUMENTS

| CA | 2304976 A1 | 5/1999 |
|---|---|---|
| CN | 1556828 A | 12/2004 |
| CN | 1706865 A | 12/2005 |
| CN | 101029131 A | 9/2007 |
| CN | 101259284 A | 9/2008 |
| CN | 104530415 A | 4/2015 |
| EP | 1496076 A1 | 12/2005 |

OTHER PUBLICATIONS

Supplementary European Search Report, EP 18 77 5559, Application No./Patent No. 18775559.0-1107 / 3604388 PCT/CN2018077229, dated Feb. 4, 2020.
International Search Report, International application No. PCT/CN2018/077229, dated May 22, 2018.
Written Opinion of the International Searching Authority, PCT/CN2018/077229, dated May 30, 2018.

* cited by examiner

*Primary Examiner* — Ana L. Woodward
(74) *Attorney, Agent, or Firm* — Flener IP & Business Law; Zareefa B. Flener

(57) ABSTRACT

Disclosed in the present invention is a method for preparing a Y-branched hydrophilic polymer carboxylic acid derivative, in particular a method for preparing a Y-branched polyethylene glycol carboxylic acid derivative having a high purity and high molecular weight. The preparation steps are simple, the product of the reaction is easy to be separated, the cost for separation is low, and the purity and yield of the product are high, facilitating the subsequent preparation of other derivatives and medicament conjugates based on the preparation of the carboxylic acid derivative, which is advantageous for industrial scale-up and commercial applications. The prepared Y-branched hydrophilic polymer carboxylic acid derivative (in particular the Y-branched polyethylene glycol carboxylic acid derivative having a high molecular weight) product has a high purity and high commercial application value, in particular in the use of the preparation of medicaments for preventing and/or treating diseases.

8 Claims, 10 Drawing Sheets

METHOD FOR PREPARING Y-BRANCHED HYDROPHILIC POLYMER CARBOXYLIC ACID DERIVATIVE

CROSS-REFERENCE TO RELATED APPLICATION

This application is a continuation application of International patent application No. PCT/CN2018/077229, filed on Feb. 26, 2018, which claims the benefit and priority of Chinese patent application No. CN201710915311.4 filed on Sep. 29, 2017 and CN201710202947.4, filed on Mar. 30, 2017 respectively, each of which is incorporated herein by reference in its entirety and for all purposes.

FIELD OF THE INVENTION

The invention relates to the technical field of polymers, in particular to a method for preparing a Y-branched hydrophilic polymer carboxylic acid derivative, in particular to a Y-branched polyethylene glycol carboxylic acid derivative having a high-purity and high molecular weight.

BACKGROUND OF THE INVENTION

Polyethylene glycol (PEG) is considered to be a polymer with a very low level of protein and cellular absorption among those known polymers, and it has good water solubility and biocompatibility, non-toxicity, non-immunity, no teratogenicity and no antigenicity. It has been widely used in the fields of drug modification and preparation production and as medical device materials.

Since 1991, after the first PEG-modified drug PEG-ADA was approved by the FDA, major pharmaceutical companies have spent a lot of energy and money in the research and development of PEG in the pharmaceutical field. In recent years, the commercially available products are PEG-somatostatin, PEG-interferon, PEG-granulocyte colony factor and the like. At present, there are dozens of PEG-modified drugs in the research or clinical trial stage.

In the field of drug modification, Y-type polyethylene glycol is a widely used polyethylene glycol, which can significantly reduce the loss of activity of modified drugs, especially in improving the clinical application of protein and polypeptide drugs. It prevents an antibody from approaching the protein drug, thereby greatly increasing the circulating half-life of the protein drug in vivo while greatly reducing its immunogenicity in vivo. For example, when the terminal group of the Y-branched PEG is a carboxyl group, it can react with an amino group, a hydroxyl group or a thiol group on a modified drug or other compound to form a covalent bond to achieve a modified linkage, and is a frequently used Y-type PEG derivative. The preparation method is performed as described in the patent CN1243779C. Specially,

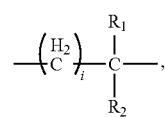

(Y-cm) can be obtained by reacting

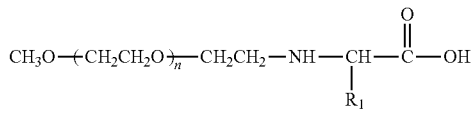

(mPEG-Gly) with

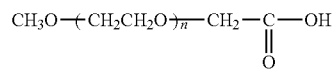

(mPEG-cm), and further purifying by ion exchange chromatography after the reaction is complete. For an anion exchange column, the more the number of —COOH groups contained in the compound, the stronger the affinity with the column is. Therefore, when the number of —COOH in the PEG structure is the same, the lower the molecular weight, the stronger the affinity with the column is. Moreover, the difference in affinity due to molecular weight would become narrower as the molecular weight further increases. However, the presence of —NH— in mPEG-gly counteracts in part the acidity of the —COOH, reducing the affinity of the impurity to the ion exchange column. The affinity of the above three compounds on the column is ranked as mPEG-Cm, mPEG-gly and Y-cm. The reaction product in the above preparation method includes the target product Y-cm and the unreacted reactants mPEG-gly and mPEG-cm. In case of high molecular weight, mPEG-gly greatly interferes with the separation, which thus reduces the purity and the yield of the target product. For example, in the preparation example of CN1243779C, the yield of the Y-type PEG product is low (only 50%), the product separation is difficult, and the cost is high, which are not favorable for industrial scale-up.

SUMMARY OF THE INVENTION

To overcome the deficiencies of the prior art, the present invention provides a process for preparing a Y-branched hydrophilic polymer carboxylic acid derivative, comprising the following reaction step:

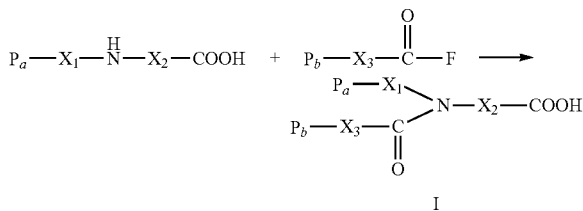

wherein $P_a$ and $P_b$ are the same or different hydrophilic polymer residues, $X_1$ and $X_3$ are linking groups, independently selected from the group consisting of: —$(CH_2)_i$—, $$-\left(\begin{matrix}H_2\\C\end{matrix}\right)_i-\underset{R_2}{\overset{R_1}{\underset{|}{\overset{|}{C}}}}-,$$

—$(CH_2)_iO$—, —$(CH_2)_iS$— and —$(CH_2)_iCO$—, or the combination thereof, i is an integer from 0 to 10, $X_2$ is a linking group selected from the group consisting of: —$(CH_2)_r$—, —$(CH_2)_rO$—, —$(CH_2)_rS$—, and

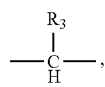

or the combination thereof, r is an integer from 0 to 10,

F is a terminal group selected from the group consisting of: a substituted or unsubstituted $C_{1-6}$ alkyl group, a substituted or unsubstituted $C_{1-6}$ alkoxy group,

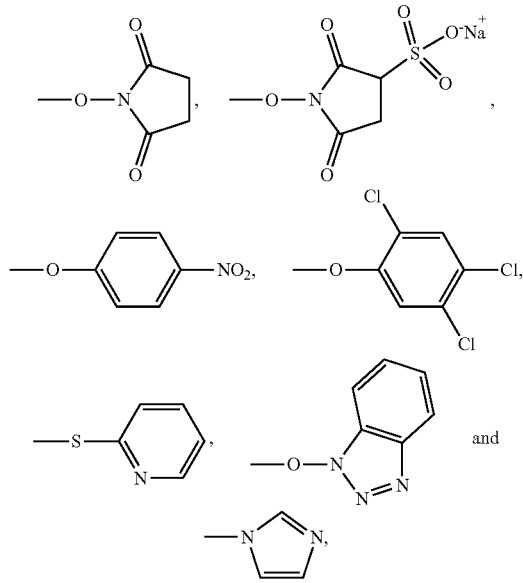

$R_1$ and $R_2$ are independently selected from the group consisting of: —H, a substituted or unsubstituted $C_{1-6}$ alkyl group, a substituted or unsubstituted $C_{1-6}$ alkoxy group, a substituted or unsubstituted $C_{3-6}$ cycloalkyl group and a substituted or unsubstituted $C_{4-10}$ alkylenecycloalkyl group, $R_3$ is selected from the group consisting of: —H, a substituted or unsubstituted $C_{1-6}$ alkyl group, a substituted or unsubstituted $C_{6-10}$ aralkyl group and a substituted or unsubstituted $C_{4-10}$ heterocyclic alkyl group, after completion of the reaction, an acid anhydride is added to continue the reaction, and then separation and purification are carried out.

The above preparation method is more suitable for preparing a higher molecular weight Y-branched hydrophilic polymer carboxylic acid derivative, and the reaction yield and product purity are higher, and it is easier to separation. In one embodiment of the present invention, the Y-branched hydrophilic polymer carboxylic acid derivative may have a molecular weight of 15 to 50 KDa (specifically 15, 16, 18, 20, 22, 24, 26, 28, 30, 32, 34, 36, 38, 40, 42, 44, 46, 48 or 50 KDa).

In one embodiment of the invention, the anhydride is an organic acid anhydride.

In one embodiment of the invention, the organic acid anhydride is selected from the group consisting of: di-tert-butyl dicarbonate (Boc anhydride), acetic anhydride, propionic anhydride, isobutyric anhydride, butyric anhydride, benzoic anhydride, and phthalic anhydride.

In a preferred embodiment of the invention, the anhydride is a Boc anhydride.

In one embodiment of the present invention, the molar ratio of the amount of the added acid anhydride to the reactant

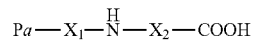

is from 0.01 to 10:1 (specifically, it may be 0.01:1, 0.1:1, 0.2:1, 0.3:1, 0.4:1, 0.5:1, 0.6:1, 0.7:1, 0.8:1, 0.9:1, 1.0:1, 1.1:1, 1.2:1, 1.3:1, 1.4:1, 1.5:1, 2.0:1, 3.0:1, 4.0:1, 5.0:1, 6.0:1, 7.0:1, 8.0:1, 9.0:1 or 10.0:1).

In one embodiment of the invention, the reaction duration after the addition of the anhydride is from 0.1 to 24 hours (specifically it may be 0.1, 1, 2, 3, 4, 5, 10, 15, 20 or 24 hours).

In one embodiment of the invention, the step of the separation and purification comprises the step of separation and purification by ion exchange chromatography.

In one embodiment of the invention, $P_a$ and $P_b$ are independently selected from residues of one or more copolymers, wherein the copolymers are selected from the group consisting of: polyethylene glycol, polypropylene glycol, polyvinyl alcohol, polytetrahydrofuran, polypropylene oxide, polybutylene oxide, polyoxetane and polypropylene morpholine.

In a preferred embodiment of the invention, $P_a$ and/or $P_b$ are/is polyethylene glycol residue(s).

In one embodiment of the present invention, $P_a$ is a polyethylene glycol residue having a structure of $R_a$—O—$(CH_2CH_2O)_m$—, and $R_a$ is selected from the group consisting of: H, $C_{1-6}$ alkyl, $C_{3-6}$ cycloalkyl and $C_{6-10}$ cycloalkyl, m is an integer from 170 to 565.

In one embodiment of the invention, $R_a$ is selected from the group consisting of H, methyl, ethyl, isopropyl, cyclopropyl, cyclobutyl, cyclohexyl and benzyl.

In a preferred embodiment of the invention, $R_a$ is H or methyl.

In one embodiment of the invention, $P_a$ is a methoxy-polyethylene glycol residue having a structure of $CH_3O$—$(CH_2CH_2O)_m$—, and m is an integer from 170 to 565.

In one embodiment of the present invention, $P_a$ may have a molecular weight of 7.5-25 KDa (specifically, it may be 7.5, 8, 9, 10, 11, 12, 13, 14, 15, 16, 17, 18, 19, 20, 21, 22, 23, 24 or 25 KDa).

In one embodiment of the present invention, $P_b$ is a polyethylene glycol residue having a structure of $R_b$—O—$(CH_2CH_2O)_n$—, and $R_b$ is selected from the group consisting of: H, $C_{1-6}$ alkyl, $C_{3-6}$ cycloalkyl and $C_{6-10}$ cycloalkyl, n is an integer from 170 to 565.

In one embodiment of the invention, $R_b$ is selected from the group consisting of H, methyl, ethyl, isopropyl, cyclopropyl, cyclobutyl, cyclohexyl and benzyl.

In a preferred embodiment of the invention, $R_b$ is H or methyl.

In one embodiment of the invention, $P_b$ is a methoxy-polyethylene glycol residue having a structure of $CH_3O$—$(CH_2CH_2O)_n$—, and n is an integer from 170 to 565.

In one embodiment of the present invention, $P_b$ may have a molecular weight of 7.5-25 KDa (specifically, it may be 7.5, 8, 9, 10, 11, 12, 13, 14, 15, 16, 17, 18, 19, 20, 21, 22, 23, 24 or 25 KDa).

In one embodiment of the invention, m and n are the equal integer.

In a preferred embodiment of the invention, the Y-branched hydrophilic polymer carboxylic acid derivative is a Y-branched polyethylene glycol carboxylic acid derivative. The reaction is as follows:

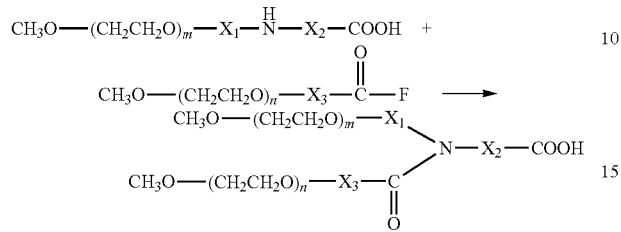

In one embodiment of the invention, $X_1$ is selected from the group consisting of: a single bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH(CH_3)$—, —$CH_2CH(CH_3)$—, —$CH_2CH_2CH(CH_3)$—, —$CH_2CH_2CH_2CH(CH_3)$—, —$CH_2CH_2CH_2CH_2CH(CH_3)$—, —$CH_2CH_2CH_2CH_2CH(CH_3)$—, —$(CH_2)_iO$— and —$(CH_2)_iCO$—, or the combination thereof, and i is an integer from 0 to 5 (such as 0, 1, 2, 3, 4 or 5).

In a preferred embodiment of the invention, said $X_1$ is —$CH_2CH_2$—.

In one embodiment of the invention, $X_3$ is selected from the group consisting of: a single bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH(CH_3)$—, —$CH_2CH(CH_3)$—, —$CH_2CH_2CH(CH_3)$—, —$CH_2CH_2CH_2CH(CH_3)$—, —$CH_2CH_2CH_2CH_2CH(CH_3)$—, —$CH_2CH_2CH_2CH_2CH(CH_3)$—, —$(CH_2)_iO$— and —$(CH_2)_iCO$—, or the combination thereof, and i is an integer from 0 to 5 (such as 0, 1, 2, 3, 4 or 5).

In a preferred embodiment of the invention, said $X_3$ is —$CH_2$—.

In an embodiment of the invention, $X_2$ is

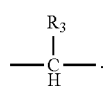

In one embodiment of the invention, $R_3$ is selected from the group consisting of: —H, —$CH_3$, —$CH_2CH(CH_3)_2$, —$CH(CH_3)CH_2CH_3$, —$CH(CH_3)_2$,

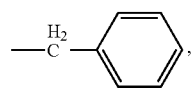

—$CH_2CH_2SCH_3$—, —$CH_2OH$, —$CH_2SH$, —$CH(OH)CH_3$,

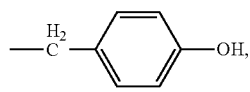

—$CH_2COOH$ and —$CH_2CH_2COOH$.

In a preferred embodiment of the invention, said $X_2$ is —$CH_2$— and —$CH(CH_3)$—.

In one embodiment of the invention, F is selected from the group consisting of: methoxy, ethoxy,

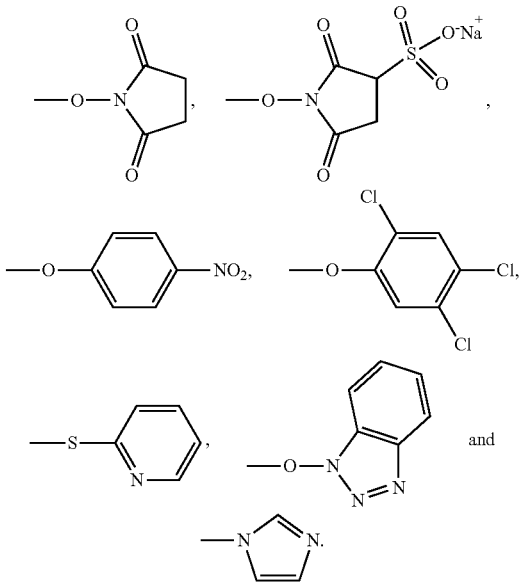

In a preferred embodiment of the invention, F is

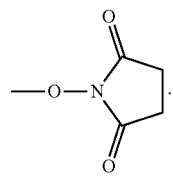

In a specific embodiment of the invention, the reaction in the preparation method is:

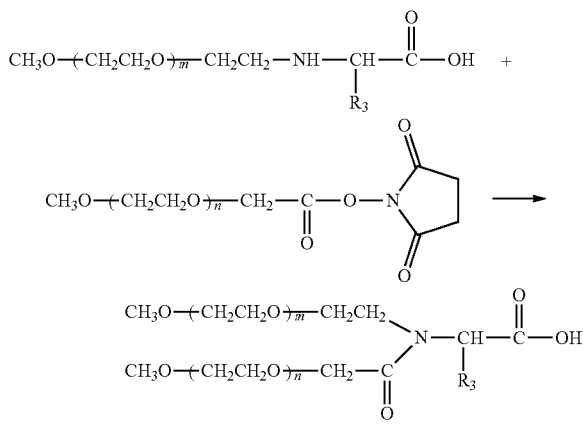

Another aspect of the present invention provides a Y-branched hydrophilic polymer carboxylic acid derivative prepared by the above method, which has the following structure:

$$P_a-X_1 \diagdown N-X_2-COOH \atop P_b-X_3-\underset{\underset{O}{\|}}{C} \diagup \qquad (I)$$

wherein, $P_a$, $P_b$, $X_1$, $X_2$ and $X_3$ have the above definitions of the present invention.

The carboxylic acid derivative has a molecular weight of 15-50 KDa (specifically it may be 15, 16, 18, 20, 22, 24, 26, 28, 30, 32, 34, 36, 38, 40, 42, 44, 46, 48 or 50 KDa).

In one embodiment of the invention, $P_a$ and $P_b$ are independently selected from residues of one or more copolymers, wherein the copolymers are selected from the group consisting of: polyethylene glycol, polypropylene glycol, polyvinyl alcohol, polytetrahydrofuran, polypropylene oxide, polybutylene oxide, polyoxetane and polypropylene morpholine.

In a preferred embodiment of the invention, $P_a$ and/or $P_b$ are/is polyethylene glycol residue(s).

In one embodiment of the present invention, $P_a$ is a polyethylene glycol residue having a structure of $R_a-O-(CH_2CH_2O)_m-$, and $R_a$ is selected from the group consisting of: H, $C_{1-6}$ alkyl, $C_{3-6}$ cycloalkyl and $C_{6-10}$ cycloalkyl, m is an integer from 170 to 565.

In one embodiment of the invention, $R_a$ is selected from the group consisting of H, methyl, ethyl, isopropyl, cyclopropyl, cyclobutyl, cyclohexyl and benzyl.

In a preferred embodiment of the invention, $R_a$ is H or methyl.

In one embodiment of the invention, $P_a$ is a methoxypolyethylene glycol residue having a structure of $CH_3O-(CH_2CH_2O)_m-$, and m is an integer from 170 to 565.

In one embodiment of the invention, $P_a$ has a molecular weight of 7.5-25 KDa (specifically it may be 7.5, 8, 9, 10, 11, 12, 13, 14, 15, 16, 17, 18, 19, 20, 21, 22, 23, 24 or 25 KDa).

In one embodiment of the present invention, $P_b$ is a polyethylene glycol residue having a structure of $R_b-O-(CH_2CH_2O)_n-$, and $R_b$ is selected from the group consisting of: H, $C_{1-6}$ alkyl, $C_{3-6}$ cycloalkyl and $C_{6-10}$ cycloalkyl, n is an integer from 170 to 565.

In one embodiment of the invention, $R_b$ is selected from the group consisting of H, methyl, ethyl, isopropyl, cyclopropyl, cyclobutyl, cyclohexyl and benzyl.

In a preferred embodiment of the invention, $R_b$ is H or methyl.

In one embodiment of the invention, $P_b$ is a methoxypolyethylene glycol residue having a structure $CH_3O-(CH_2CH_2O)_n-$, and n is an integer from 170 to 565.

In one embodiment of the present invention, $P_b$ may have a molecular weight of 7.5-25 KDa (specifically, it may be 7.5, 8, 9, 10, 11, 12, 13, 14, 15, 16, 17, 18, 19, 20, 21, 22, 23, 24 or 25 KDa).

In one embodiment of the present invention, the Y-branched hydrophilic polymer carboxylic acid derivative is a Y-branched polyethylene glycol carboxylic acid derivative having the following structure:

$$CH_3O-(CH_2CH_2O)_m-X_1 \diagdown N-X_2-COOH \atop CH_3O-(CH_2CH_2O)_n-X_3-\underset{\underset{O}{\|}}{C} \diagup \qquad (II)$$

In one embodiment of the invention, $X_1$ is selected from the group consisting of: a single bond, $-CH_2-$, $-CH_2CH_2-$, $-CH_2CH_2CH_2-$, $-CH_2CH_2CH_2CH_2-$, $-CH_2CH_2CH_2CH_2CH_2-$, $-CH(CH_3)-$, $-CH_2CH(CH_3)-$, $-CH_2CH_2CH(CH_3)-$, $-CH_2CH_2CH_2CH(CH_3)-$, $-CH_2CH_2CH_2CH_2CH(CH_3)-$, $-CH_2CH_2CH_2CH_2CH_2CH(CH_3)-$, $-(CH_2)_iO-$ and $-(CH_2)_iCO-$, or the combination thereof, and i is an integer from 0 to 5 (such as 0, 1, 2, 3, 4 or 5).

In a preferred embodiment of the invention, $X_1$ is $-CH_2CH_2-$.

In one embodiment of the invention, $X_3$ is selected from the group consisting of: a single bond, $-CH_2-$, $-CH_2CH_2-$, $-CH_2CH_2CH_2-$, $-CH_2CH_2CH_2CH_2-$, $-CH_2CH_2CH_2CH_2CH_2-$, $-CH(CH_3)-$, $-CH_2CH(CH_3)-$, $-CH_2CH_2CH(CH_3)-$, $-CH_2CH_2CH_2CH(CH_3)-$, $-CH_2CH_2CH_2CH_2CH(CH_3)-$, $-CH_2CH_2CH_2CH_2CH_2CH(CH_3)-$, $-(CH_2)_iO-$ and $-(CH_2)_iCO-$, or the combination thereof, and i is an integer from 0 to 5 (such as 0, 1, 2, 3, 4 or 5).

In a preferred embodiment of the invention, $X_3$ is $-CH_2-$.

In an embodiment of the invention, $X_2$ is $$-\underset{H}{\overset{R_3}{\underset{|}{C}}}-.$$

In one embodiment of the invention, the carboxylic acid derivative has the structure of:

$$CH_3O-(CH_2CH_2O)_m-CH_2CH_2 \diagdown N-CH-\underset{\underset{}{\overset{O}{\|}}}{C}-OH \atop CH_3O-(CH_2CH_2O)_n-CH_2-\underset{\underset{O}{\|}}{C} \diagup \; | \atop R_3 \qquad (III)$$

In one embodiment of the invention, $R_3$ is selected from the group consisting of: $-H$, $-CH_3$, $-CH_2CH(CH_3)_2$, $-CH(CH_3)CH_2CH_3$, $-CH(CH_3)_2$, $$-\overset{H_2}{C}-\!\!\!\bigcirc\!\!\!,$$

$-CH_2CH_2SCH_3-$, $-CH_2OH$, $-CH_2SH$, $-CH(OH)CH_3$, $$-\overset{H_2}{C}-\!\!\!\bigcirc\!\!\!-OH,$$

$-CH_2COOH$ and $-CH_2CH_2COOH$.

In a preferred embodiment of the invention, said $R_3$ is $-H$ or $-CH_3$.

In one embodiment of the invention, m and n are equal integers.

Another aspect of the present invention also provides a Y-branched hydrophilic polymer derivative derived from the above carboxylic acid, which has the following structure:

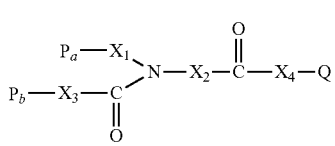

(IV)

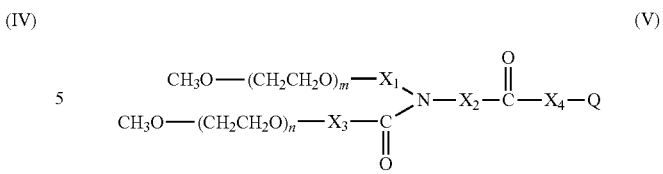

(V)

wherein $P_a$, $P_b$, $X_1$, $X_2$, $X_3$ have the above definition of the invention, $X_4$ is a linking group selected from: $-(CH_2)_j-$, $-(CH_2)_jO-$, $-(CH_2)_jS-$, $-(CH_2)_jCO-$, $-(CH_2)_jNH-$, $-(CH_2)_jCONH-$ and $-(CH_2)_jNHCO-$, or the combination thereof, and j is an integer from 0 to 10, Q is a terminal group selected from the group consisting of: $C_{1-6}$ alkoxy, hydroxy, amino, carboxy, thiol, ester, keto, aldehyde, orthopyridyl disulfide, azide, hydrazide, alkynyl, silane, maleimidyl and succinimidyl.

In one embodiment of the invention, the derivative may have a molecular weight of 15-50 KDa (specifically it may be 15, 16, 18, 20, 22, 24, 26, 28, 30, 32, 34, 36, 38, 40, 42, 44, 46, 48 or 50 KDa).

In one embodiment of the invention, $P_a$ and $P_b$ are independently a residue of one or more copolymers selected from the group consisting of polyethylene glycol, polypropylene glycol, polyvinyl alcohol, polytetrahydrofuran, polypropylene oxide, polybutylene oxide, polyoxetane and polypropylene morpholine In a preferred embodiment of the invention, $P_a$ and/or $P_b$ are/is polyethylene glycol residue(s).

In one embodiment of the present invention, $P_a$ is a polyethylene glycol residue having a structure of $R_a-O-(CH_2CH_2O)_m-$, and $R_a$ is selected from the group consisting of: H, $C_{1-6}$ alkyl, $C_{3-6}$ cycloalkyl and $C_{6-10}$ cycloalkyl, and m is an integer from 170 to 565.

In one embodiment of the invention, $R_a$ is selected from the group consisting of H, methyl, ethyl, isopropyl, cyclopropyl, cyclobutyl, cyclohexyl and benzyl.

In a preferred embodiment of the invention, $R_a$ is H or methyl.

In one embodiment of the invention, $P_a$ is a methoxy-polyethylene glycol residue having a structure of $CH_3O-(CH_2CH_2O)_m-$, and m is an integer from 170 to 565.

In one embodiment of the invention, $P_a$ has a molecular weight of 7.5-25 KDa (specifically it may be 7.5, 8, 9, 10, 11, 12, 13, 14, 15, 16, 17, 18, 19, 20, 21, 22, 23, 24 or 25 KDa).

In one embodiment of the present invention, $P_b$ is a polyethylene glycol residue having a structure of $R_b-O-(CH_2CH_2O)_n-$, and $R_b$ is selected from the group consisting of: H, $C_{1-6}$ alkyl, $C_{3-6}$ cycloalkyl and $C_{6-10}$ cycloalkyl, and n is an integer from 170 to 565.

In one embodiment of the invention, $R_b$ is selected from the group consisting of H, methyl, ethyl, isopropyl, cyclopropyl, cyclobutyl, cyclohexyl and benzyl.

In a preferred embodiment of the invention, $R_b$ is H or methyl.

In one embodiment of the invention, $P_b$ is a methoxy-polyethylene glycol residue having a structure of $CH_3O-(CH_2CH_2O)_n-$, and n is an integer from 170 to 565.

In one embodiment of the present invention, $P_b$ may have a molecular weight of 7.5-25 KDa (specifically, it may be 7.5, 8, 9, 10, 11, 12, 13, 14, 15, 16, 17, 18, 19, 20, 21, 22, 23, 24 or 25 KDa).

In one embodiment of the invention, the Y-branched hydrophilic polymer derivative is a Y-branched polyethylene glycol derivative having the following structure:

In one embodiment of the invention, $X_4$ is selected from the group consisting of: a single bond, $-CH_2-$, $-CH_2CH_2-$, $-CH_2CH_2CH_2-$, $-CH_2CH_2CH_2CH_2-$, $-CH_2CH_2CH_2CH_2CH_2-$, $-(CH_2)_jCO-$, $-(CH_2)_jNH-$, $-(CH_2)_jCONH-$ and $-(CH_2)_jNHCO-$, or the combination thereof, and j is an integer from 0 to 5 (e.g., 0, 1, 2, 3, 4 or 5).

In a preferred embodiment of the invention, $X_4$ is selected from the group consisting of: a single bond, $-CH_2-$, $-CH_2CH_2-$, $-CH_2CH_2CH_2-$, $-CH_2NH-$, $-CH_2CH_2NH-$, $-CH_2CH_2CH_2NH-$, $-CH_2CONH-$, $-CH_2CH_2CONH-$ and $-CH_2CH_2CH_2CONH-$, or the combination thereof.

In one embodiment of the invention, Q is selected from the group consisting of: $-OH$, $-SH$, $-C\equiv CH$, $-NH_2$, $-COOH$, $-CHO$,

and $-N_3$.

In a preferred embodiment of the invention, the Y-branched hydrophilic polymer derivative has the following structure:

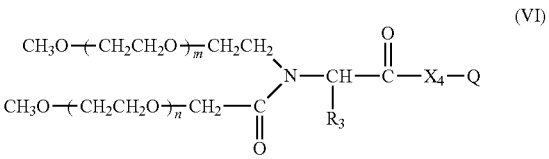

(VI)

In one embodiment of the invention, $R_3$ is selected from the group consisting of: $-H$, $-CH_3$, $-CH_2CH(CH_3)_2$, $-CH(CH_3)CH_2CH_3$, $-CH(CH_3)_2$,

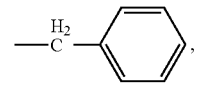

$-CH_2CH_2SCH_3-$, $-CH_2OH$, $-CH_2SH$, $-CH(OH)CH_3$,

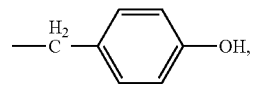

$-CH_2COOH$ and $-CH_2CH_2COOH$.

In a preferred embodiment of the invention, said $R_3$ is —H or —$CH_3$.

In one embodiment of the invention, m and n are equal integers.

Another aspect of the present invention provides a process for preparing the above Y-branched hydrophilic polymer derivative, which comprises the steps in the preparation method of the above Y-branched hydrophilic polymer carboxylic acid derivative.

Another aspect of the present invention provides a use of the above Y-branched hydrophilic polymer carboxylic acid derivative or Y-branched hydrophilic polymer derivative in the modification of a drug.

Another aspect of the present invention provides a conjugate of the above Y-branched hydrophilic polymer carboxylic acid derivative or Y-branched hydrophilic polymer derivative of the present invention with a drug.

In one embodiment of the invention, the drug is selected from the group consisting of amino acids, polypeptides, proteins, carbohydrate, organic acids, alkaloids, flavonoids, quinones, terpenoids, phenylpropanoid phenols, steroids, and glycoside drugs.

Another aspect of the present invention provides the use of the method for preparing the above-mentioned Y-branched hydrophilic polymer carboxylic acid derivative of the present invention, in the manufacture of pharmaceutical composition containing the above-mentioned Y-branched hydrophilic polymer carboxylic acid derivative.

Another aspect of the present invention provides the use of the method for preparing the above-mentioned Y-branched hydrophilic polymer carboxylic acid derivative of the present invention, in the manufacture of the above Y-branched hydrophilic polymer derivative, or the pharmaceutical conjugate thereof.

Another aspect of the invention also provides a pharmaceutical composition comprising the above conjugate of the invention and, optionally, a pharmaceutically acceptable carrier or excipient.

Another aspect of the present invention provides the use of the Y-branched hydrophilic polymer carboxylic acid derivative, the Y-branched polyethylene glycol derivative, or the pharmaceutical conjugate thereof or the pharmaceutical composition thereof, in the manufacture of a medicament for treating a disease.

The preparation method of the Y-branched hydrophilic polymer carboxylic acid derivative (especially Y-branched polyethylene glycol carboxylic acid derivative having high-purity and high molecular weight) as provided by the invention has simple preparation steps, and meanwhile the reaction product is easy to separate, the cost for separation is low, and the purity and yield of the product are high, which facilitate the subsequent preparation of other derivatives and medicament conjugates based on the carboxylic acid derivative, and are advantageous for industrial scale-up and commercial applications. The prepared Y-branched hydrophilic polymer carboxylic acid derivative (in particular the Y-branched polyethylene glycol carboxylic acid derivative having a high molecular weight) product has a high purity and high commercial application value, in particular in the use thereof in the manufacture of medicaments for preventing and/or treating diseases.

DETAILED DESCRIPTION OF THE INVENTION

Figure 1:
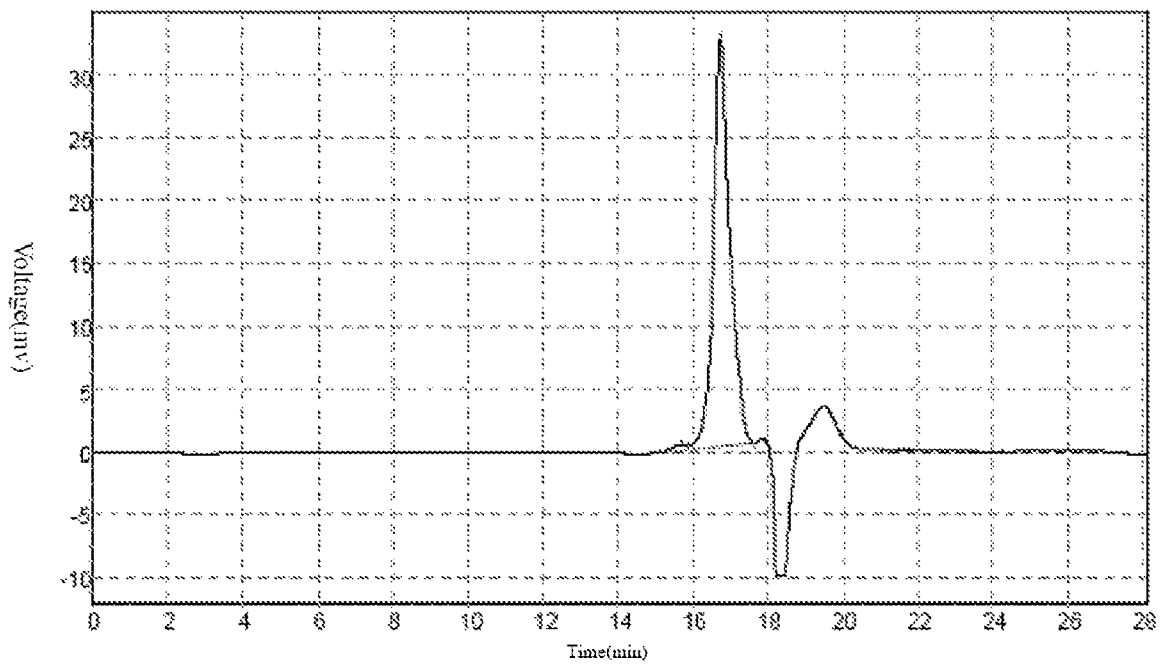
FIG. 1 is a GFC chromatogram of the crude product before column separation in Example 1 of the present invention.

Unless defined otherwise, all technical and scientific terms used in the present invention have the same meaning as commonly understood by one of ordinary skill in the art to which this invention belongs.

"Alkyl" refers to a hydrocarbon chain radical that is linear or branched and free of unsaturated bonds, and which is linked to the rest of the molecule by a single bond. The $C_1$-$C_6$ alkyl means an alkyl having 1 to 6 carbon atoms, such as methyl, ethyl, n-propyl, isopropyl, n-butyl, isobutyl, t-butyl, n-pentyl, isopentyl, neopentyl, tert-amyl, n-hexyl, isohexyl and the like. If the alkyl group is substituted by a cycloalkyl group, it is correspondingly a "cycloalkylalkyl" radical, such as cyclopropylmethyl, cyclopropylethyl, cyclobutylmethyl, cyclopentylmethyl, cyclohexylmethyl, etc. If the alkyl group is substituted by an aryl group, it is correspondingly an "aralkyl" radical, such as benzyl, benzhydryl or phenethyl. If the alkyl group is substituted by a heterocyclic group, it is correspondingly a "heterocyclylalkyl" radical.

"Alkoxy" means a substituent formed by substituting the hydrogen in hydroxy group with an alkyl group, and $C_1$-$C_6$ alkoxy group means an alkoxy group having 1 to 6 carbon atoms, such as methoxy or ethoxy, propoxy, butoxy, and the like.

"Cycloalkyl" means an alicyclic hydrocarbon, such as those containing 1 to 4 monocyclic and/or fused rings. It may contain 3 to 18 carbon atoms, preferably 3 to 10 carbon atoms, such as cyclopropyl, cyclohexyl or adamantyl and the like. $C_3$-$C_6$ cycloalkyl in the present invention means a cycloalkyl having 3 to 6 carbon atoms, such as cyclopropyl, cyclobutyl, cyclopentyl and cyclohexyl.

A "substituted" group as used in the present invention refers to a group which is substituted at one or more of available sites by one or more suitable groups. Specifically, for example, a substituted alkyl group refers to an alkyl group in which one or more hydrogens are substituted by one or more suitable groups such as an alkyl group (e.g., C1-6 alkyl group, particularly C1-3 alkyl, such as methyl, ethyl, propyl or isopropyl), alkoxy (such as C1-6 alkoxy, especially C1-3 alkoxy, such as methoxy, ethoxy or propoxy), alkenyl (such as C1-6 alkenyl, especially C1-3 alkenyl, such as vinyl), alkynyl (such as C1-6 alkynyl, especially C1-3 alkynyl, such as propynyl), cycloalkyl(such as C3-6 cycloalkyl, such as cyclopropyl, cyclobutyl, cyclopentyl or cyclohexyl), aryl(such as C6-12 aryl, especially phenyl), aryloxy(such as phenoxyl), alkaryl (such as benzyl), heterocyclic group (such as C3-12 heterocyclic group, which may contain 1, 2 or 3 hetero atoms, wherein the hetero atom is/are one or more selected from the group consisting of N, O and S atoms), halogen (F, Cl, Br or I), cyano (—CN), hydroxy (—OH), nitro (—$NO_2$), azide (—$N_3$), acyl (such as alkanoyl, especially C1-6 alkanoyl such as formyl, acetyl or the like; or amide group), amine group (e.g., primary amino, secondary amino), carboxyl(—COOH), ester or the like.

In addition, some specific groups and their chemical structures involved in the present invention correspond to the following: hydroxyl group, —OH; amino group, —$NH_2$; carboxyl group,

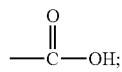

thiol, —SH; ester group,

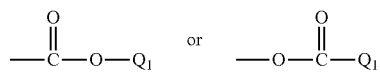

(where $Q_1$ may be an alkyl, aryl or heterocyclic group such as methyl, ethyl, n-propyl, t-butyl, -maleimidyl, succinimidyl,

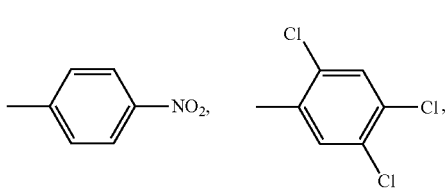

etc.; keto group,

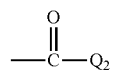

(wherein $Q_2$ may be a substituted or unsubstituted alkyl, aryl, heterocyclic group such as a substituted or unsubstituted methyl, ethyl, n-propyl, etc.); aldehyde group, —CHO; orthopyridyl disulfide,

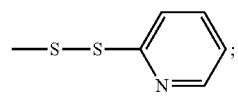

azido,

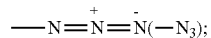

hydrazide,

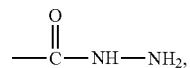

alkynyl, —C≡CH; silane,

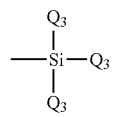

(wherein $Q_3$ may be the same or different alkyl or alkoxy, such as methyl, ethyl, propyl, butyl, pentyl, methoxy, ethoxy, propoxy, butoxy, etc., preferably, $Q_3$ is methyl, ethyl, n-propyl, methoxy, ethoxy, n-propoxy, etc.); maleimidyl,

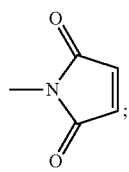

succinimide,

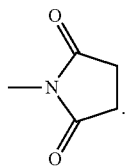

In the definition of a linking group in the present invention, the "combination" means a group formed by linking two or more of the listed linking groups by a chemical bond. For example, the combination of —$(CH_2)_j$— and —$(CH_2)_j$NHCO— may be —$(CH_2)_j$NHCO$(CH_2)_j$— and specifically, the combination of —$CH_2$— and —$CH_2CH_2$NHCO— may be —$CH_2CH_2$NHCOCH$_2$—, —$CH_2CH_2CH_2$NHCO—.

The "combination" is used to define the chemical structure of the linking group, and does not involve the preparation steps, the order of linking groups in the combination, etc.

The technical solutions of the present invention will be described clearly and completely with reference to the Examples of the present invention. It is obvious that the described Examples are only a part of the embodiments of the present invention, and not all the possible embodiments. All other embodiments obtained by a person of ordinary skill in the art based on the embodiments of the present invention are within the protection scope of the present invention.

Example 1: Synthesis of Y-Branched Polyethylene Glycol-Acetic Acid (Molecular Weight 4000) (Prior Art)

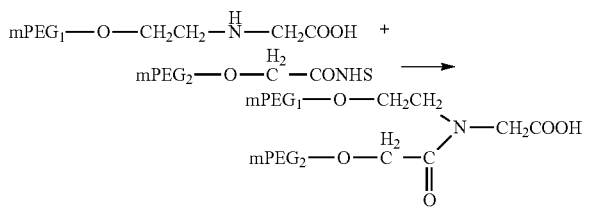

Y-branched polyethylene glycol-acetic acid having a molecular weight of 4000 was prepared by the synthesis method of Example 5 in Patent CN1243779C: 10 g of polyethylene glycol monomethyl ether-aminoacetic acid (mPEG-Gly) having a molecular weight of 2000 and 10 g methoxy polyethylene glycol succinimidyl acetate (mPEG-OCH$_2$CO—NHS) having a molecular weight of 2000 were dissolved in 200 ml of dichloromethane, 2.5 ml of triethylamine was added to the solution, and the reaction was carried out overnight at room temperature, and the solvent was concentrated by rotary evaporation. Diethyl ether was added to the residue, and the precipitate was collected by filtration, dried in vacuum, and purified by ion-exchange chromatography column. The target product was collected when the peak height of the target product is over 5 mv and the collection was stopped when the peak height of the target product is less than 5 mv, as monitored by gel filtration chromatography (GFC).

The GFC chromatogram of the crude product before column separation is shown in FIG. 1. The results are shown in Table 1:

TABLE 1

| | Analysis Results | | | |
|---|---|---|---|---|
| Peak No(s) | Retention Time | Peak Height(s) | Peak Area(s) | Content |
| 1 | 15.673 | 414.977 | 11847.592 | 1.1696 |
| 2 | 16.372 | 32425.010 | 1001135.563 | 98.8304 |
| Total | | 32839.987 | 1012983.154 | 100.0000 |

Figure 2:
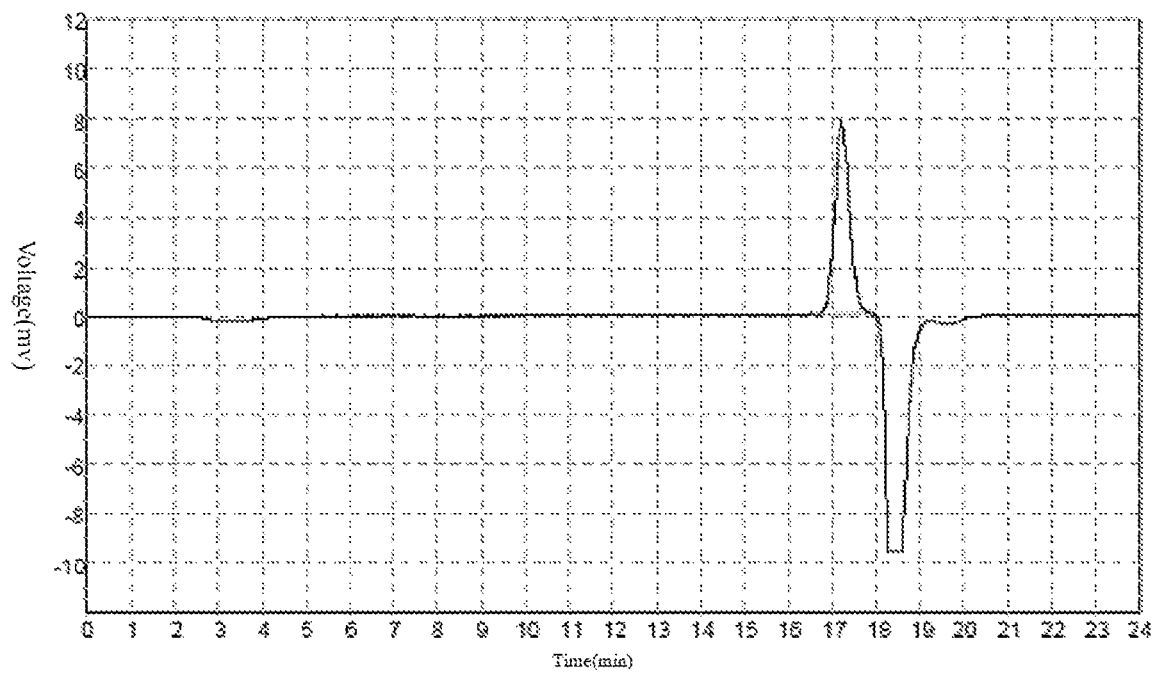
FIG. 2 is a GFC chromatogram at the collection starting point in Example 1 of the present invention.

The GHC chromatogram at the collection starting point is shown in FIG. 2, and the results are analyzed as shown in Table 2:

TABLE 2

| | Analysis Results | | | |
|---|---|---|---|---|
| Peak No(s) | Retention Time | Peak Height(s) | Peak Area(s) | Content |
| 1 | 17.217 | 7592.177 | 182213.703 | 100.0000 |
| Total | | 7592.177 | 182213.703 | 100.0000 |

Figure 3:
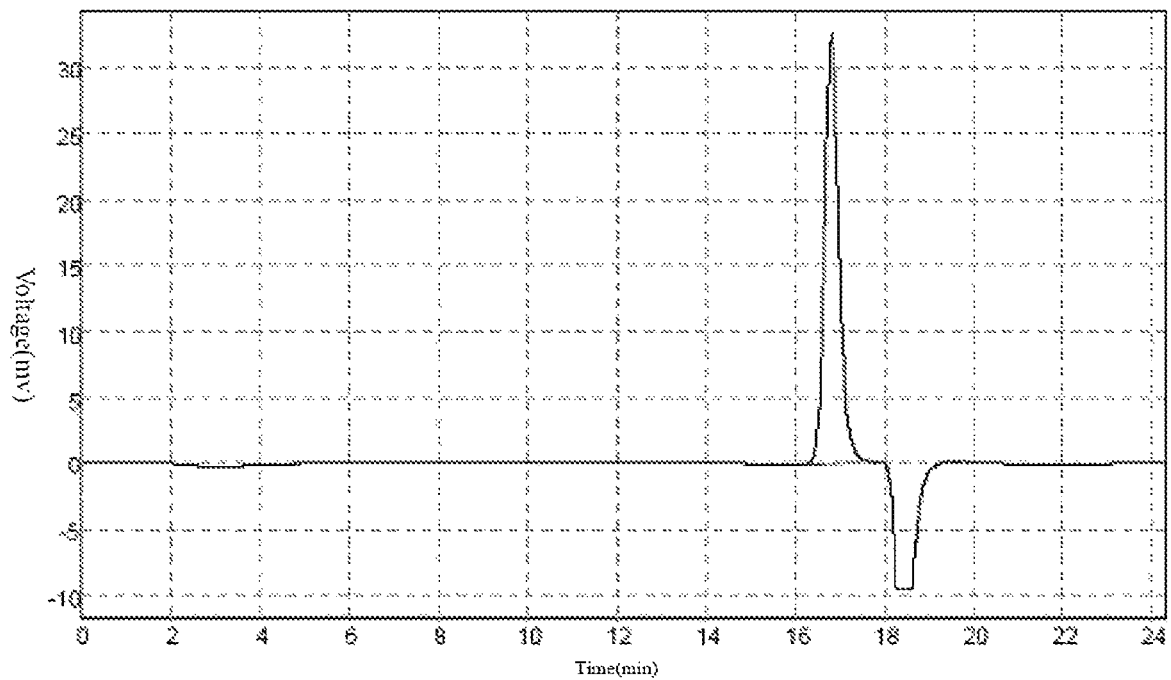
FIG. 3 is a GFC chromatogram at peak point in Example 1 of the present invention.

The GFC chromatogram at the peak point is shown in FIG. 3, and the results are analyzed as shown in Table 3:

TABLE 3

| | Analysis Results Table | | | |
|---|---|---|---|---|
| Peak No(s) | Retention Time | Peak Height(s) | Peak Area(s) | Content |
| 1 | 16.803 | 32242.705 | 737351.500 | 100.0000 |
| Total | | 32242.705 | 737351.500 | 100.0000 |

Figure 4:
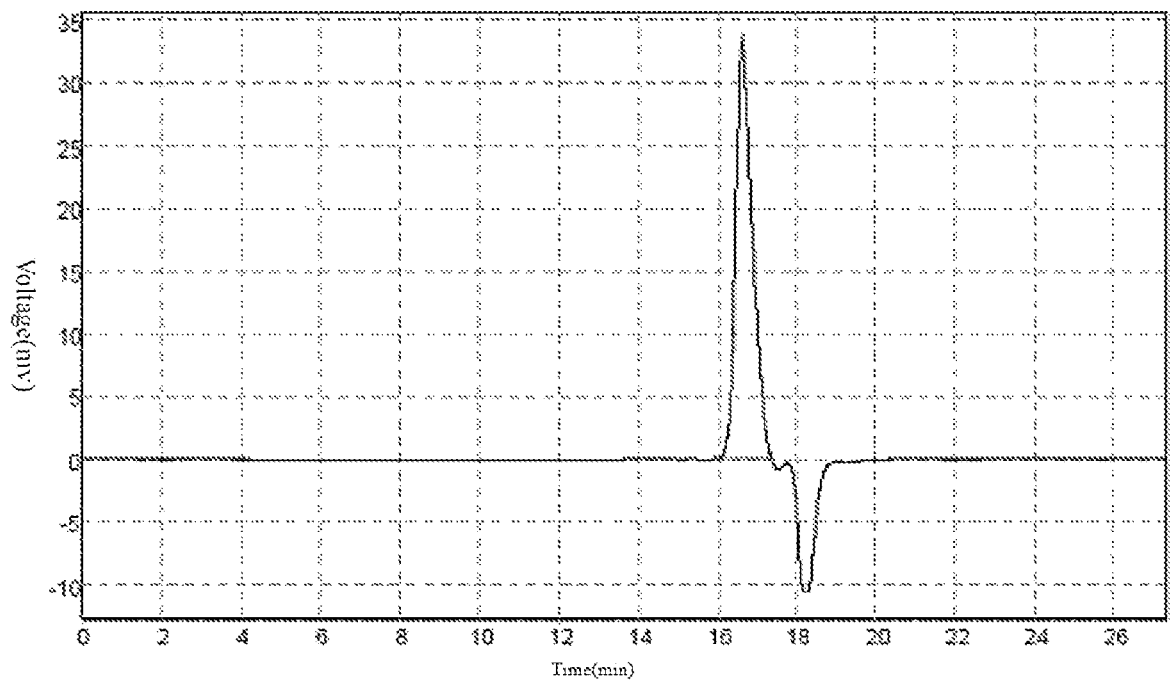
FIG. 4 is a GFC chromatogram of the product after column separation in Example 1 of the present invention.

The GFC chromatogram of the product after column separation is shown in FIG. 4, and the results are shown in Table 4:

TABLE 4

| | Analysis Results Table | | | |
|---|---|---|---|---|
| Peak No(s) | Retention Time | Peak Height(s) | Peak Area(s) | Content |
| 1 | 16.625 | 33298.703 | 972173.063 | 100.0000 |
| Total | | 33298.703 | 972173.063 | 100.0000 |

It can be seen from the above-mentioned spectrums and analysis results that in the case of low molecular weight, the crude product with higher purity can be obtained by using the prior art, and accordingly, the purification process also goes smoothly, and the purity of the target product at the collection starting point has reached 100%. Therefore, no further process improvement is necessary.

Example 2: Synthesis of Y-Branched Polyethylene Glycol-Acetic Acid (Molecular Weight 20000) (Prior Art)

The Y-branched polyethylene glycol-acetic acid having a molecular weight of 20,000 was prepared by the synthesis method of Example 5 in Patent CN1243779C: 10 g of polyethylene glycol monomethyl ether-aminoacetic acid (mPEG-Gly) having a molecular weight of 10,000 and 10 g methoxy polyethylene glycol succinimidyl acetate (mPEG-OCH$_2$CO—NHS) having a molecular weight of 10,000 were dissolved in 200 ml of dichloromethane, 0.11 ml of triethylamine was added to the solution, and the reaction was carried out overnight at room temperature, and the solvent was concentrated by rotary evaporation. Diethyl ether was added to the residue, and the precipitate was collected by filtration, dried in vacuum, purified by ion-exchange chromatography column. The target product was collected when the peak height of the target product is over 5 mv and the collection was stopped when the peak height of the target product is less than 5 mv, as monitored by gel filtration chromatography (GFC).

Figure 5:
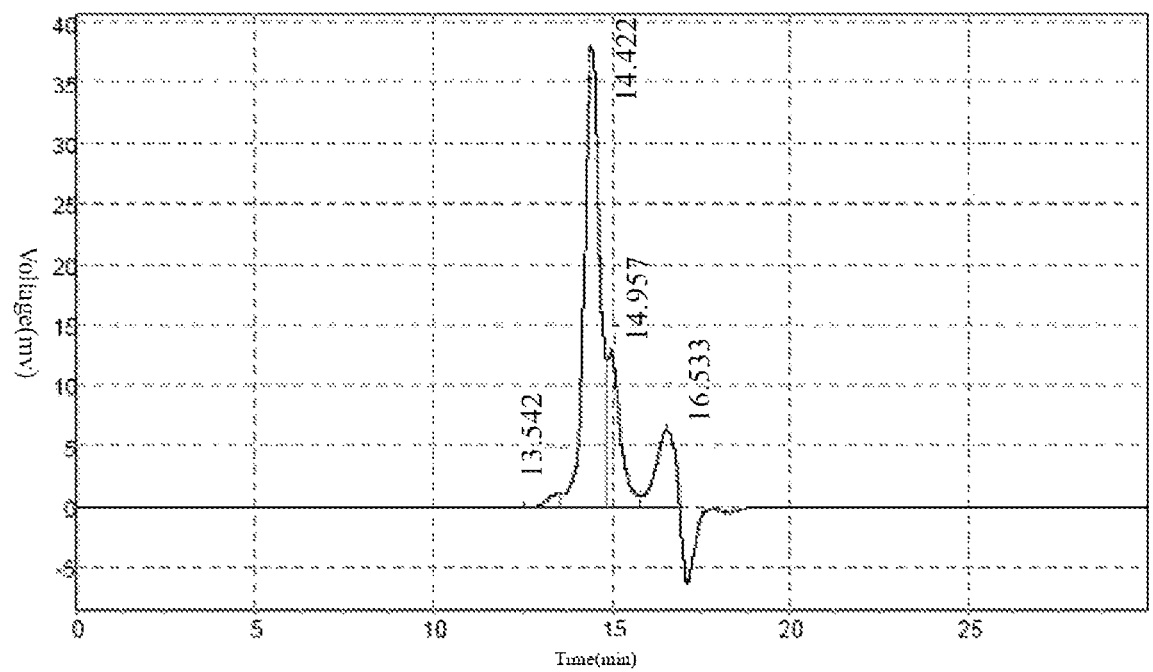
FIG. 5 is a GFC chromatogram of the crude product before column separation in Example 2 of the present invention.

The chromatogram of the crude GFC before column separation is shown in FIG. 5, and the results are shown in Table 5:

TABLE 5

| | Analysis Results | | | |
|---|---|---|---|---|
| Peak No(s) | Retention Time | Peak Height(s) | Peak Area(s) | Content |
| 1 | 13.542 | 1022.931 | 24926.658 | 1.4350 |
| 2 | 14.422 | 38444.813 | 1144562.250 | 65.8933 |
| 3 | 14.957 | 12657.612 | 327516.594 | 18.8554 |
| 4 | 16.533 | 6417.722 | 239988.859 | 13.8163 |
| Total | | 58543.077 | 1736994.361 | 100.0000 |

Figure 6:
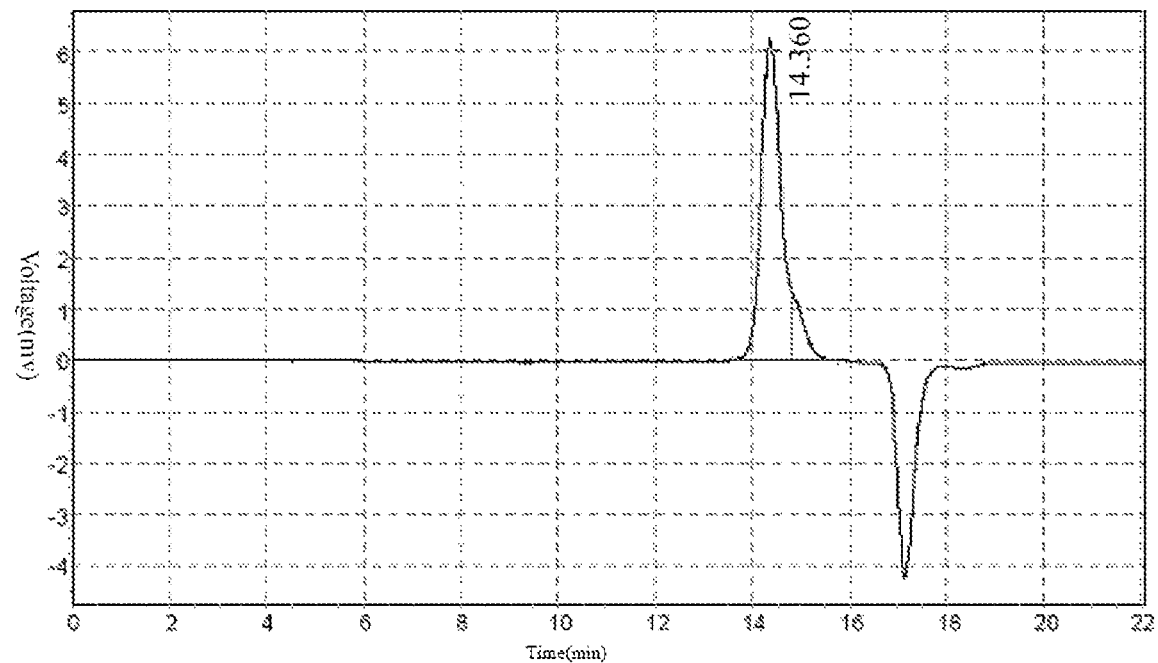
FIG. 6 is a GFC chromatogram at the collection starting point in Example 2 of the present invention.

The GFC chromatogram at the collection starting point is shown in FIG. 6, and the results are analyzed as shown in Table 6:

TABLE 6

| | Analysis Results | | | |
|---|---|---|---|---|
| Peak No(s) | Retention Time | Peak Height(s) | Peak Area(s) | Content |
| 1 | 14.360 | 6247.910 | 175948.938 | 89.2082 |
| 2 | 14.360 | 1307.907 | 21285.078 | 10.7918 |
| Total | | 7582.817 | 197234.016 | 100.0000 |

Figure 7:
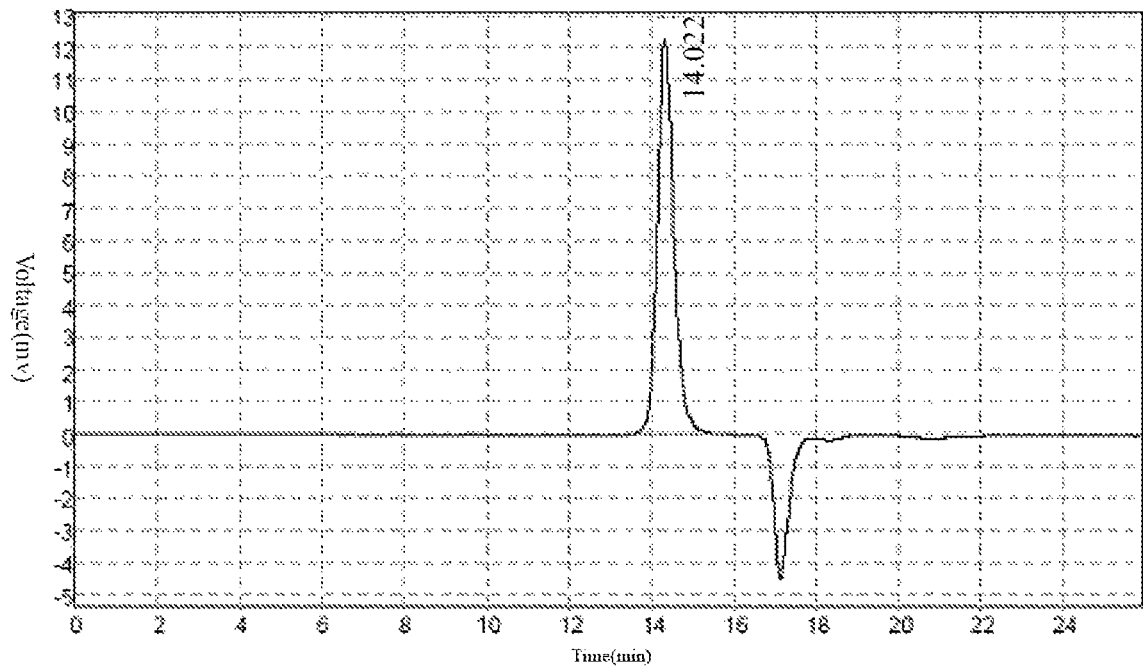
FIG. 7 is a GFC chromatogram at peak point in Example 2 of the present invention.

The GFC chromatogram at the peak point is shown in FIG. 7, and the results are analyzed as shown in Table 7:

TABLE 7

| Analysis Results | | | | |
|---|---|---|---|---|
| Peak No(s) | Retention Time | Peak Height(s) | Peak Area(s) | Content |
| 1 | 14.322 | 12284.006 | 343873.844 | 100.0000 |
| Total | | 12284.006 | 343873.844 | 100.0000 |

Figure 8:
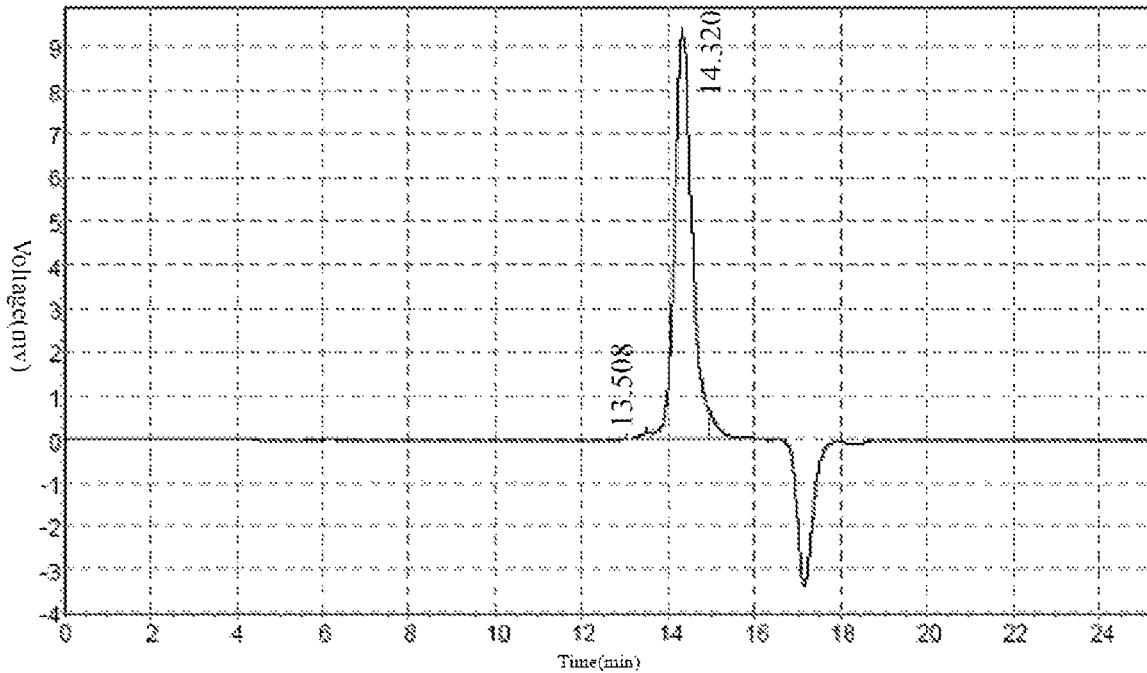
FIG. 8 is a GFC chromatogram of the product after column separation in Example 2 of the present invention.

The GFC chromatogram of the product after column separation is shown in FIG. 8, and the results are shown in Table 8:

TABLE 8

| Analysis Results | | | | |
|---|---|---|---|---|
| Peak No(s) | Retention Time | Peak Height(s) | Peak Area(s) | Content |
| 1 | 13.508 | 137.165 | 2951.444 | 1.0913 |
| 2 | 14.320 | 9269.781 | 260161.203 | 96.1946 |
| 3 | 14.320 | 625.753 | 7340.421 | 2.7141 |
| Total | | 10032.699 | 270453.069 | 100.0000 |

Example 3: Synthesis of the Y-Branched Polyethylene Glycol-Acetic Acid (Molecular Weight 20000) (Method of the Present Invention)

The reaction of mPEG-Gly with mPEG-OCH$_2$CO—NHS was carried out according to Example 2. After the reaction at room temperature overnight, BOC anhydride was added, and allowed to react for 3 hours. The solvent was concentrated by rotary evaporation, diethyl ether was added to the residue, and the precipitate was collected by filtration, dried in vacuum, purified by ion-exchange chromatography column. The target product was collected when the peak height of the target product is over 5 mv and the collection was stopped when the peak height of the target product is less than 5 mv, as monitored by gel filtration chromatography (GFC).

Figure 9:
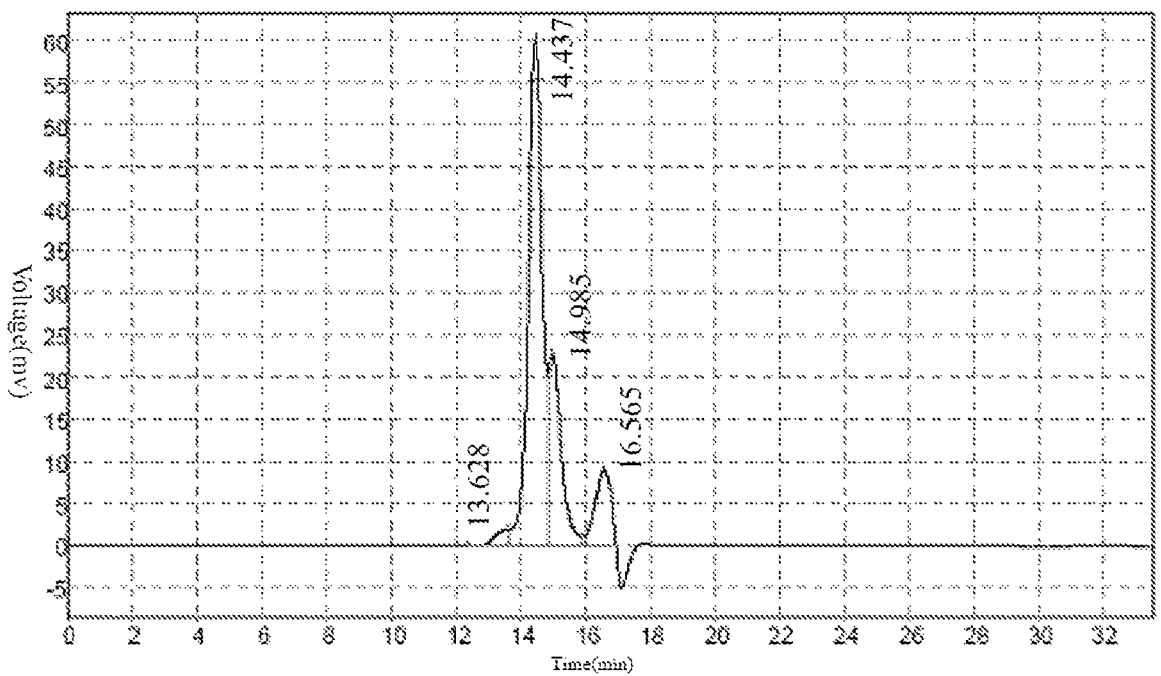
FIG. 9 is a GFC chromatogram of the crude product before column separation in Example 3 of the present invention.

The GFC chromatogram of the crude product before column is shown in FIG. 9, and the results are shown in Table 9.

TABLE 9

| Analysis Results | | | | |
|---|---|---|---|---|
| Peak No(s) | Retention Time | Peak Height(s) | Peak Area(s) | Content |
| 1 | 13.628 | 1750.234 | 49552.457 | 1.7936 |
| 2 | 14.437 | 59970.328 | 1791721.875 | 64.8528 |
| 3 | 14.985 | 22595.111 | 610309.625 | 22.0906 |
| 4 | 16.565 | 8841.112 | 311167.094 | 11.2629 |
| Total | | 93156.785 | 2762751.051 | 100.0000 |

Figure 10:
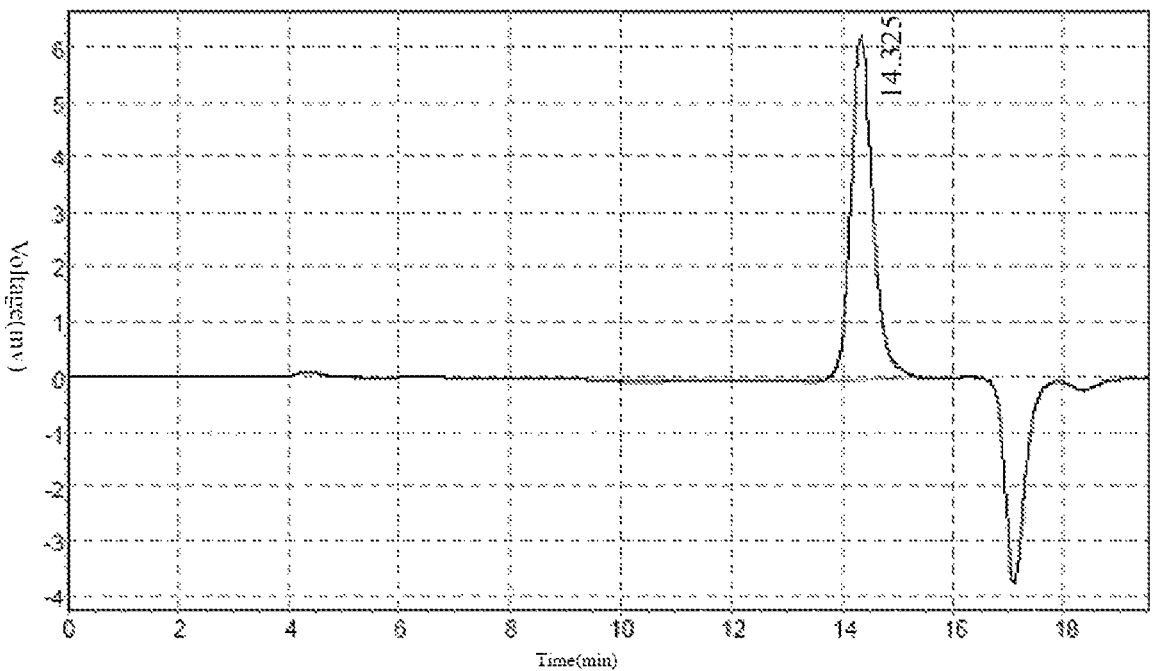
FIG. 10 is a GFC chromatogram at the collection starting point in Example 3 of the present invention.

The GFC chromatogram at the collection starting point is shown in FIG. 10, and the results are analyzed as shown in Table 10:

TABLE 10

| Analysis Results | | | | |
|---|---|---|---|---|
| Peak No(s) | Retention Time | Peak Height(s) | Peak Area(s) | Content |
| 1 | 14.325 | 6200.920 | 171336.391 | 100.0000 |
| Total | | 6200.920 | 171336.391 | 100.0000 |

Figure 11:
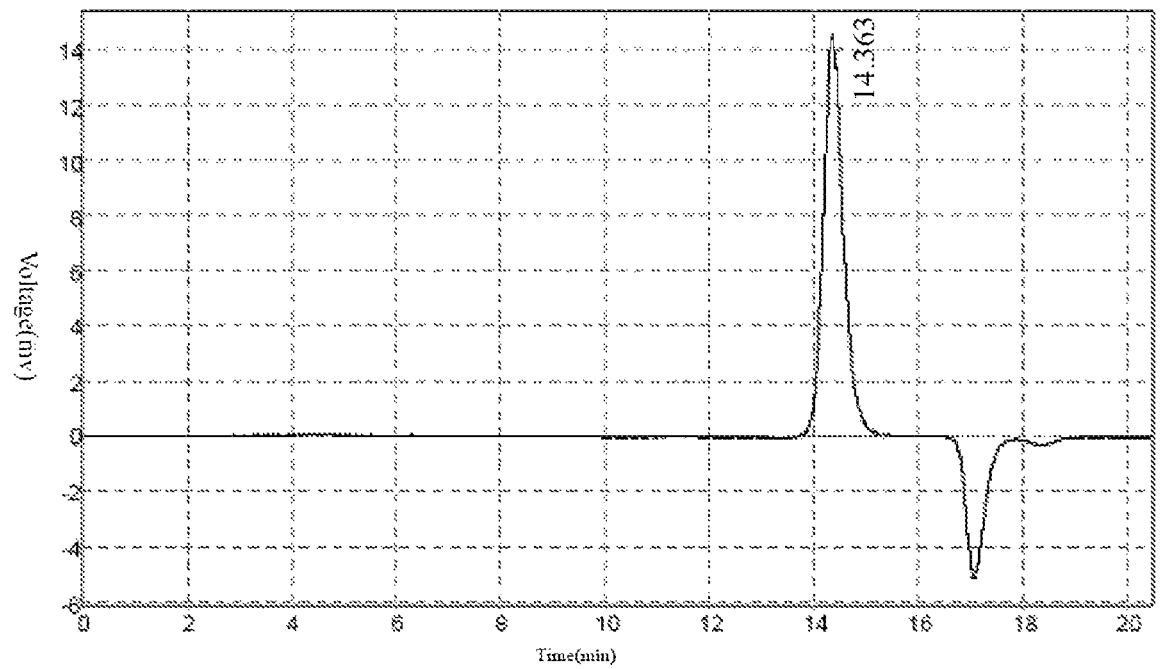
FIG. 11 is a GFC chromatogram at peak point in Example 3 of the present invention.

The GFC chromatogram at peak point is shown in FIG. 11, and the results are analyzed as shown in Table 11:

TABLE 11

Analysis Results

| Peak No(s) | Retention Time | Peak Height(s) | Peak Area(s) | Content |
|---|---|---|---|---|
| 1 | 14.363 | 14437.756 | 391282.094 | 100.0000 |
| Total | | 14437.756 | 391282.094 | 100.0000 |

Figure 12:
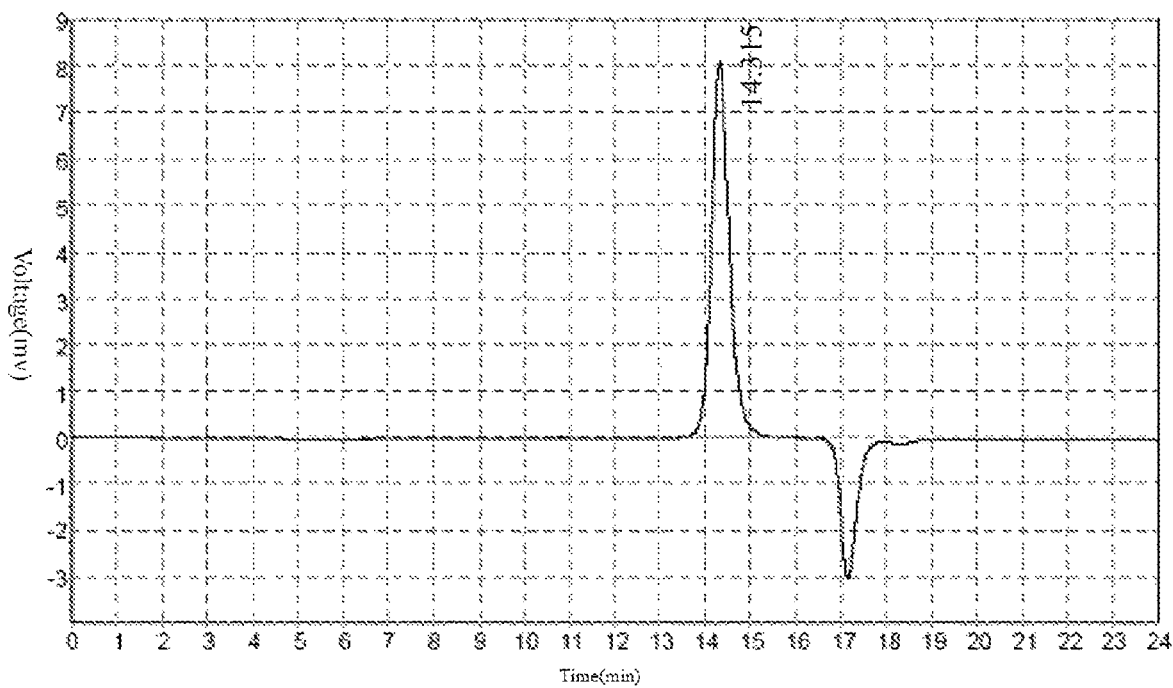
FIG. 12 is a GFC chromatogram of the product after column separation in Example 3 of the present invention.

The GFC chromatogram of the product after column separation is shown in FIG. 12, and the results are shown in Table 12:

TABLE 12

Analysis Results

| Peak No(s) | Retention Time | Peak Height(s) | Peak Area(s) | Content |
|---|---|---|---|---|
| 1 | 14.315 | 8015.271 | 224045.094 | 100.0000 |
| Total | | 8015.271 | 224045.094 | 100.0000 |

It can be seen from the comparison of Examples 2 and 3 that in the preparation of the Y-branched polyethylene glycol-acetic acid product having a molecular weight of 20,000, the application of the prior art may have a certain adverse effect on the subsequent purification process. The purity of the target product is 89.2% when the collection standard is just reached, and the final product purity can only reach 96.2%. However, for this molecular weight, the purity of the target product can still reach 100% when the concentration is at the peak. Therefore, if a product with a purity of 100% is to be obtained by the prior art, it is necessary to discard some of the target products in the column separation process, which affects the yielding rate.

In comparison, the target product having a purity of 100% can be obtained at the starting point of the column collection by the method of the present invention, and thus the purification efficiency is improved.

Example 4: Synthesis of Y-Branched Polyethylene Glycol-Acetic Acid (Molecular Weight 44000) (Prior Art)

The Y-branched polyethylene glycol-acetic acid having a molecular weight of 44,000 was prepared by the synthesis method of Example 5 of Patent CN1243779C: 10 g of polyethylene glycol monomethyl ether-aminoacetic acid (mPEG-Gly) having a molecular weight of 22000 and 10 g of methoxy polyethylene glycol succinimidyl acetate (mPEG-OCH$_2$CO—NHS) having a molecular weight of 22000 were dissolved in 200 ml of dichloromethane, 0.23 ml of triethylamine was added to the solution, and the reaction was carried out overnight at room temperature, and the solvent was concentrated by rotary evaporation. Diethyl ether was added to the residue, and the precipitate was collected by filtration, dried in vacuum, purified by ion-exchange chromatography column. The target product was collected when the peak height of the target product is over 5 mv and the collection was stopped when the peak height of the target product is less than 5 mv, as monitored by gel filtration chromatography (GFC).

Figure 13:
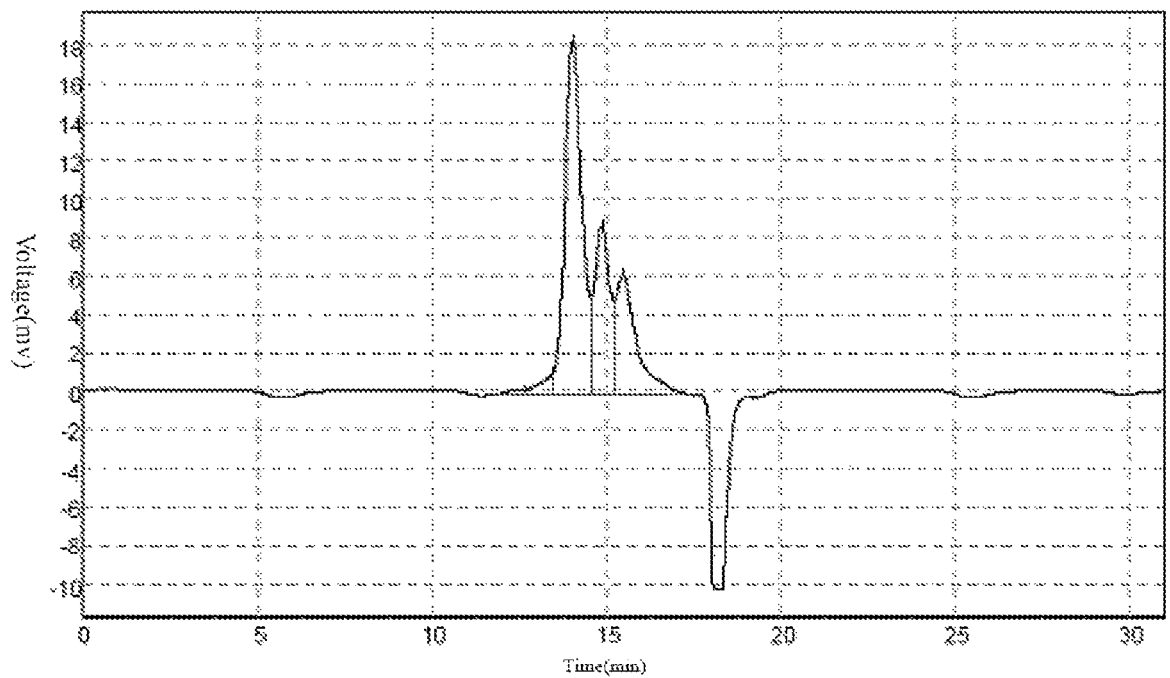
FIG. 13 is a GFC chromatogram of the crude product before column separation in Example 4 of the present invention.

The GFC chromatogram of the crude product before column separation is shown in FIG. 13, and the results are shown in Table 13:

TABLE 13

Analysis Results

| Peak No(s) | Retention Time | Peak Height(s) | Peak Area(s) | Content |
|---|---|---|---|---|
| 1 | 12.632 | 216.849 | 5853.640 | 0.4888 |
| 2 | 13.463 | 1105.972 | 28798.725 | 2.4049 |
| 3 | 14.022 | 18448.070 | 632011.188 | 52.7769 |
| 4 | 14.858 | 8744.209 | 264832.563 | 22.1152 |
| 5 | 15.463 | 6208.482 | 266019.656 | 22.2143 |
| Total | | 34723.582 | 1197515.771 | 100.0000 |

Figure 14:
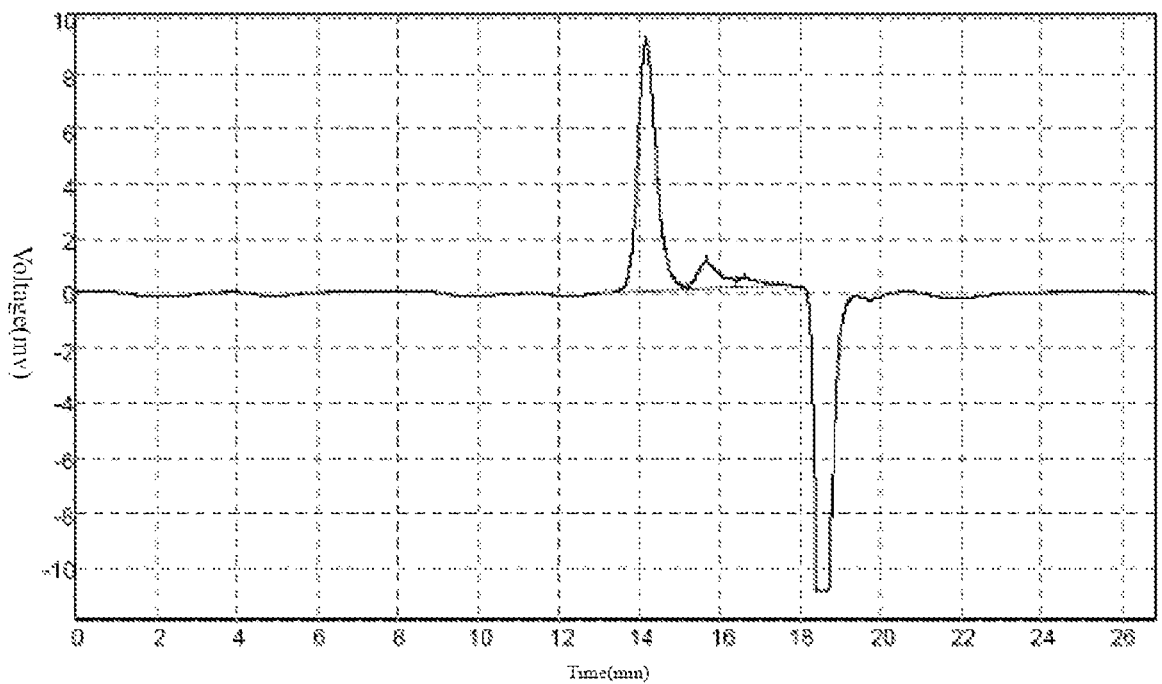
FIG. 14 is a GFC chromatogram at the collection starting point in Example 4 of the present invention.

The GFC chromatogram at the collection starting point is shown in FIG. 14, and the results are analyzed as shown in Table 14:

TABLE 14

Analysis Results

| Peak No(s) | Retention Time | Peak Height(s) | Peak Area(s) | Content |
|---|---|---|---|---|
| 1 | 14.162 | 9122.315 | 295129.031 | 84.7402 |
| 2 | 15.660 | 997.469 | 40453.988 | 11.6155 |
| 3 | 16.647 | 300.680 | 12692.063 | 3.6443 |
| Total | | 10420.465 | 348275.082 | 100.0000 |

Figure 15:
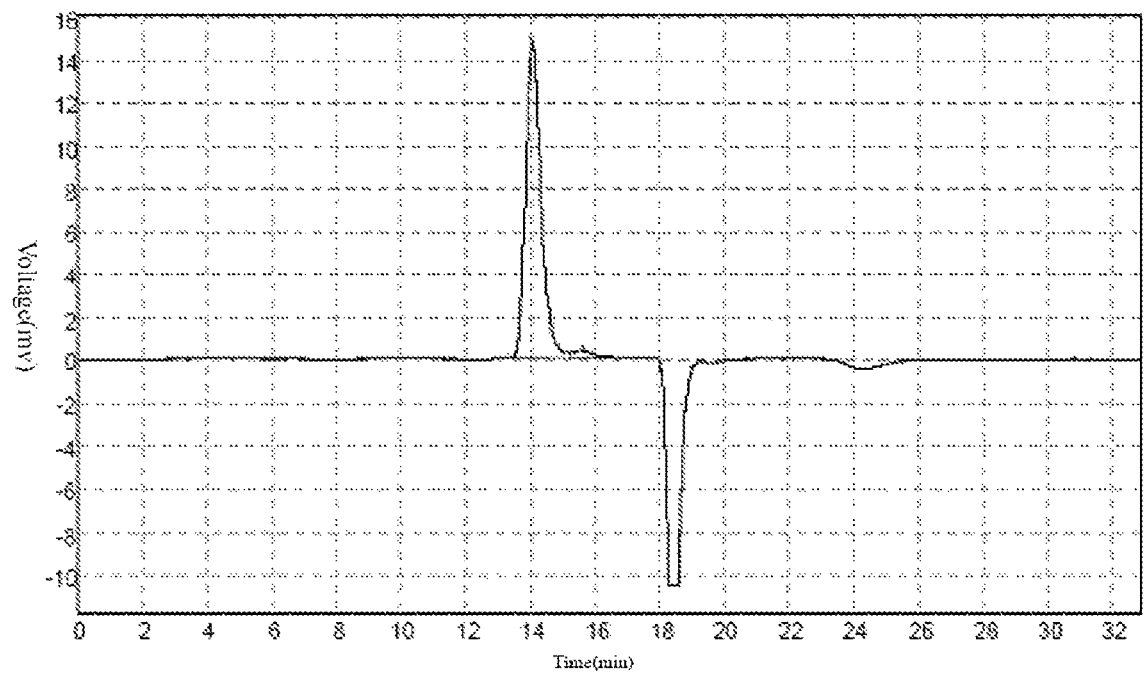
FIG. 15 is a GFC chromatogram at peak point in Example 4 of the present invention.

The GFC chromatogram at peak point is shown in FIG. 15, and the results are analyzed as shown in Table 15:

TABLE 15

Analysis Results

| Peak No(s) | Retention Time | Peak Height(s) | Peak Area(s) | Content |
|---|---|---|---|---|
| 1 | 14.050 | 14704.603 | 493573.531 | 97.1771 |
| 2 | 15.583 | 339.659 | 14337.928 | 2.8229 |
| Total | | 15044.262 | 507911.459 | 100.0000 |

Figure 16:
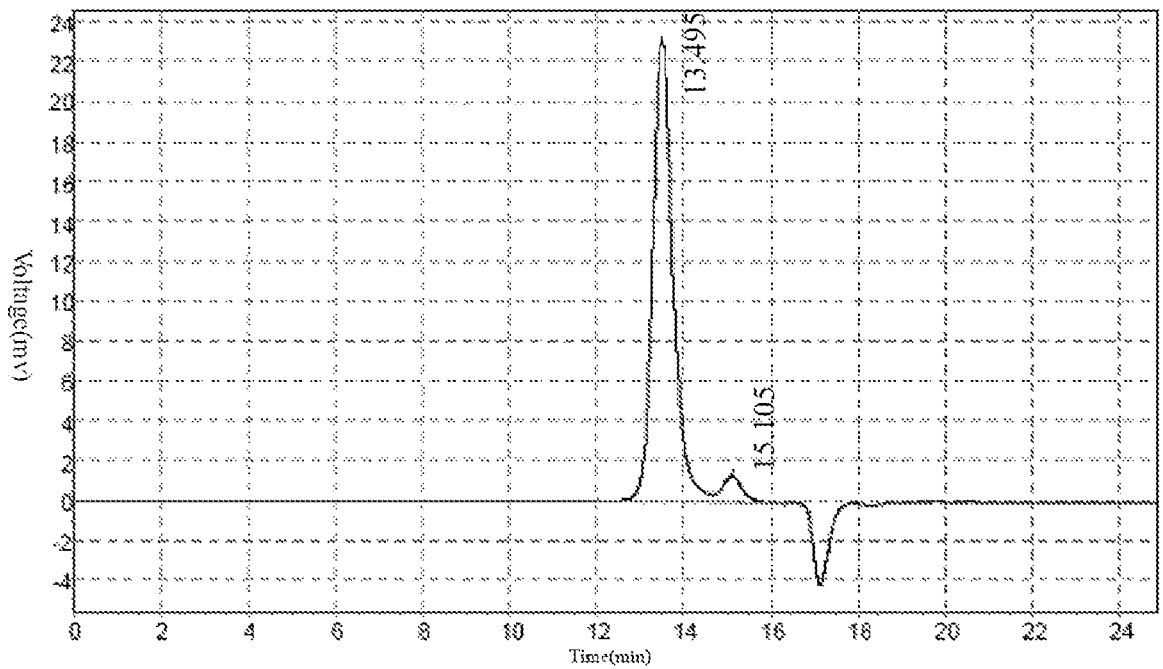
FIG. 16 is a GFC chromatogram of the product after column separation in Example 4 of the present invention.

The GFC chromatogram of product after column separation is shown in FIG. 16, and the results are analyzed as shown in Table 16:

TABLE 16

Analysis Results

| Peak No(s) | Retention Time | Peak Height(s) | Peak Area(s) | Content |
|---|---|---|---|---|
| 1 | 13.495 | 23209.838 | 757190.563 | 94.5259 |
| 2 | 15.105 | 1324.436 | 43849.547 | 5.4741 |
| Total | | 24534.274 | 801040.109 | 100.0000 |

Example 5: Synthesis of the Y-Branched Polyethylene Glycol-Acetic Acid (Molecular Weight 44000) (Method of the Present Invention)

The reaction of mPEG-Gly with mPEG-OCH$_2$CO—NHS was carried out according to Example 4.

After reaction at room temperature overnight, BOC anhydride was added, and allowed to react for 3 hours. The solvent was concentrated by rotary evaporation, diethyl ether was added to the residue, and the precipitate was collected by filtration, dried in vacuum, purified by ion-exchange chromatography column. The target product was collected when the peak height of the target product is over 5 mv and the collection was stopped when the peak height of the target product is less than 5 mv, as monitored by gel filtration chromatography (GFC).

Figure 17:
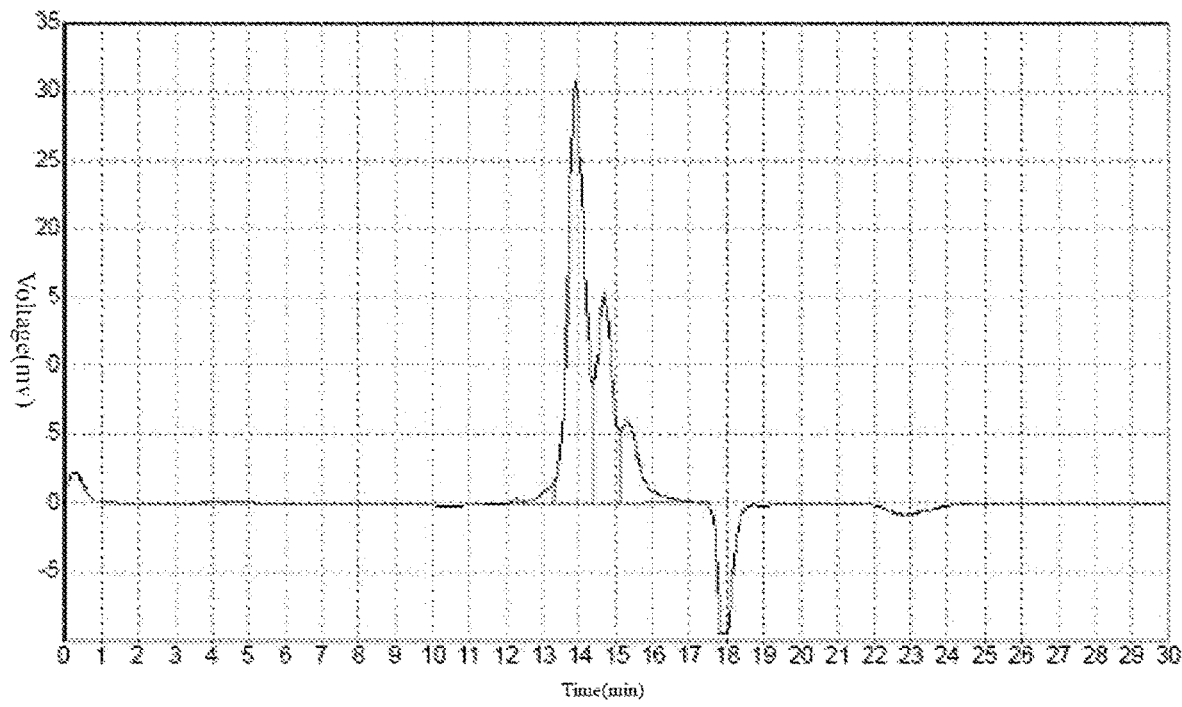
FIG. 17 is a GFC chromatogram of the crude product before column separation in Example 5 of the present invention.

The GFC chromatogram of the crude product before column separation is shown in FIG. 17, and the results are shown in Table 17:

TABLE 17

Analysis Results

| Peak No(s) | Retention Time | Peak Height(s) | Peak Area(s) | Content |
|---|---|---|---|---|
| 1 | 12.253 | 231.301 | 6857.705 | 0.3944 |
| 2 | 13.293 | 1547.840 | 35137.719 | 2.0208 |
| 3 | 13.887 | 30439.711 | 1028076.500 | 59.1249 |
| 4 | 14.672 | 15103.429 | 457737.344 | 26.3246 |
| 5 | 15.302 | 5943.133 | 211012.344 | 12.1354 |
| Total | | 53265.413 | 1738821.611 | 100.0000 |

Figure 18:
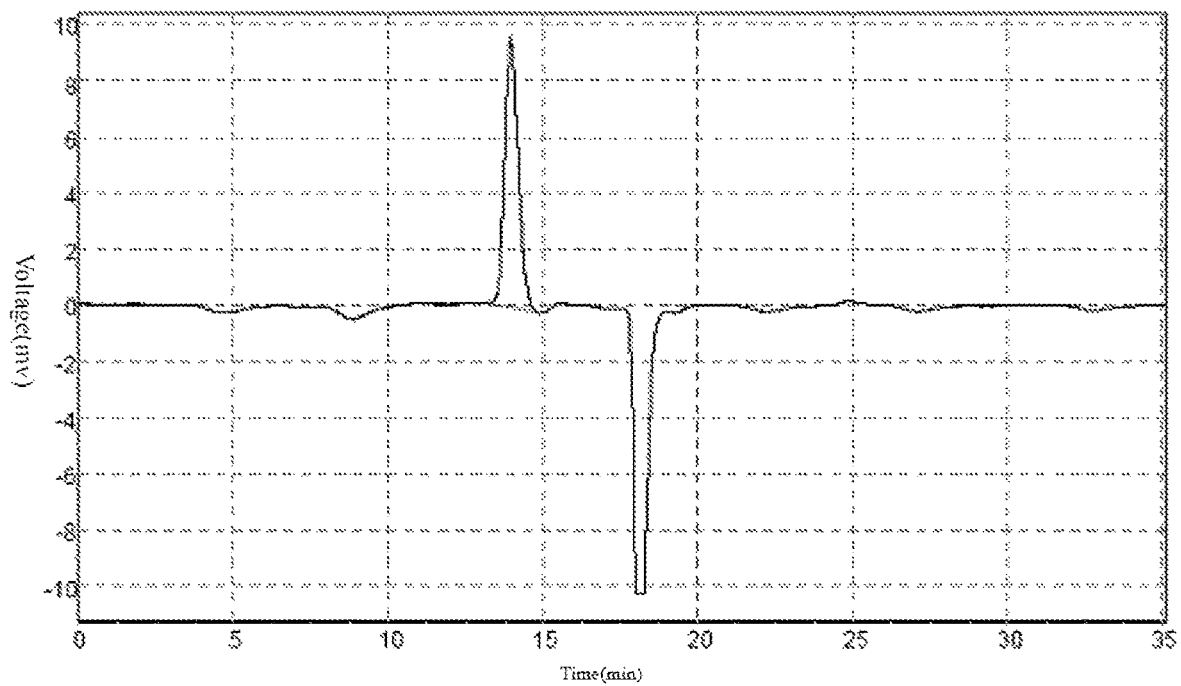
FIG. 18 is a GFC chromatogram at the collection starting point in Example 5 of the present invention.

The GFC chromatogram of the collection starting point is shown in FIG. 18, and the results are analyzed as shown in Table 18:

TABLE 18

Analysis Results

| Peak No(s) | Retention Time | Peak Height(s) | Peak Area(s) | Content |
|---|---|---|---|---|
| 1 | 13.945 | 9493.703 | 290778.813 | 100.0000 |
| Total | | 9493.703 | 290778.813 | 100.0000 |

Figure 19:
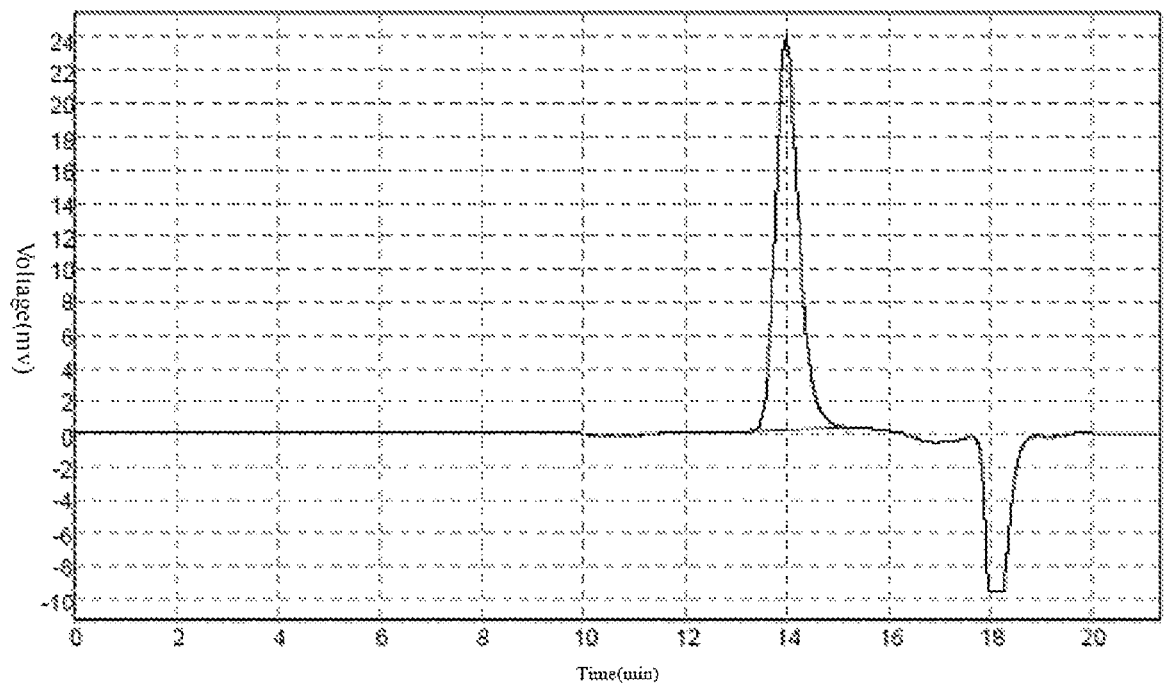
FIG. 19 is a GFC chromatogram at peak point in Example 5 of the present invention.

The GFC chromatogram of peak point is shown in FIG. 19, and the results are analyzed as shown in Table 19:

TABLE 19

Analysis Results

| Peak No(s) | Retention Time | Peak Height(s) | Peak Area(s) | Content |
|---|---|---|---|---|
| 1 | 13.975 | 23614.199 | 761874.313 | 100.0000 |
| Total | | 23614.199 | 761874.313 | 100.0000 |

Figure 20:
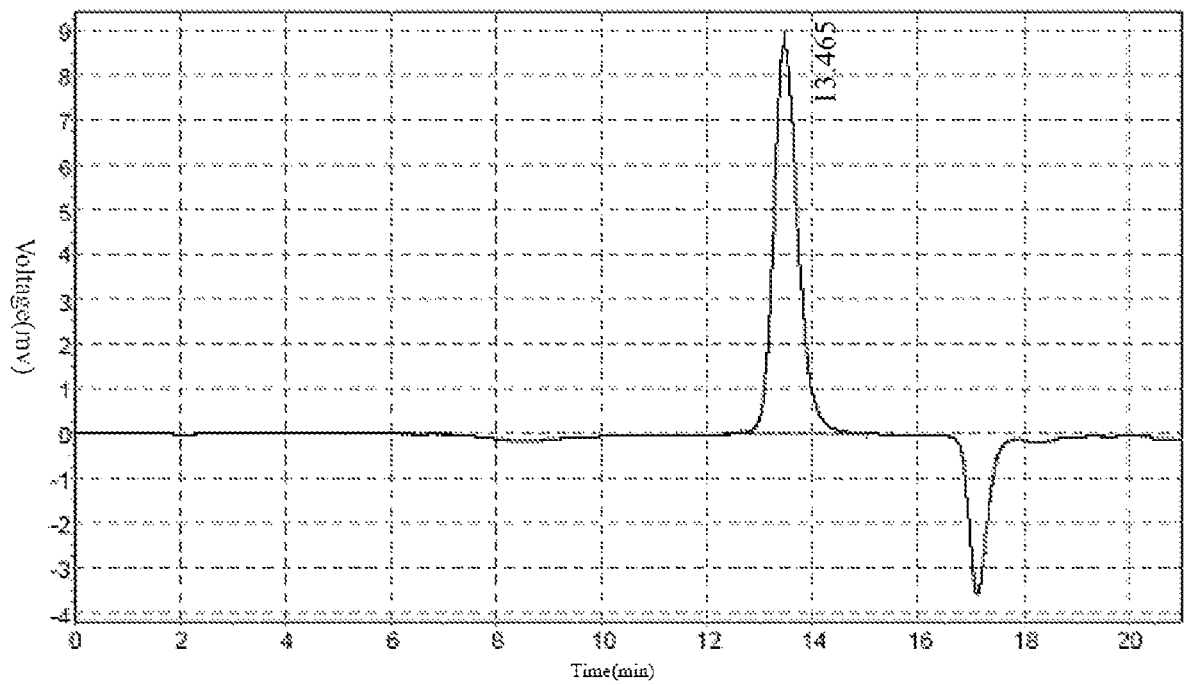
FIG. 20 is a GFC chromatogram of the product after column separation in Example 5 of the present invention.

The GFC chromatogram of the product after column separation is shown in FIG. 20, and the results are analyzed as shown in Table 20:

TABLE 20

Analysis Results

| Peak No(s) | Retention Time | Peak Height(s) | Peak Area(s) | Content |
|---|---|---|---|---|
| 1 | 13.465 | 8814.110 | 278729.406 | 100.0000 |
| Total | | 8814.110 | 278729.406 | 100.0000 |

It can be seen from the comparison of Examples 4 and 5 that in the preparation of the Y-branched polyethylene glycol-acetic acid product having a molecular weight of 44,000, the application of the prior art would have serious effects on the subsequent purification process. The purity of the target product is 84.7% when the collection standard is just reached, the purity at the peak is only 97.2% and the purity of the final product can only reach 94.5%. Thus, high purity products could not be obtained by this prior method.

In comparison, the target product having a purity of 100% can be obtained at the starting point of the column collection by the method of the present invention, and thus the purification efficiency is significantly improved.

As can be seen from the above examples, the effect of the prior art on product purification will gradually increase with increasing molecular weight, and the method of the present invention can significantly improve purification yield and product purity for high molecular weight products.

The above is only the preferred embodiment of the present invention, and is not intended to limit the present invention. Any modifications, equivalent substitutions, etc., which are within the spirit and principles of the present invention, should be included in the scope of the present invention.

The invention claimed is:

1. A method for preparing a Y-branched hydrophilic polymer carboxylic acid derivative, the method comprising the following reaction step:

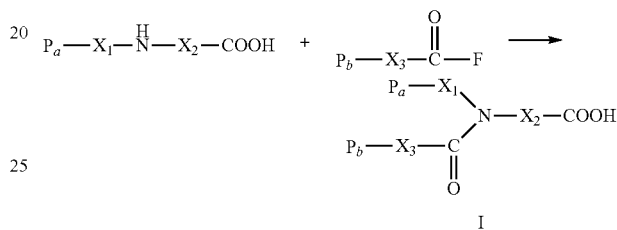

wherein $P_a$ and $P_b$ are the same or different hydrophilic polymer residues, $X_1$ and $X_3$ are linking groups, independently selected from the group consisting of: —$(CH_2)_i$—,

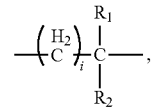

—$(CH_2)_iO$—, —$(CH_2)_iS$— and —$(CH_2)_iCO$—, or the combination of two or more of these selections, i is an integer from 0 to 10, $X_2$ is a linking group selected from the group consisting of: —$(CH_2)_r$—, —$(CH_2)_rO$—, —$(CH_2)_rS$—, and

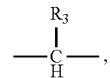

or the combination of two or more of these selections, r is an integer from 0 to 10, F is a terminal group selected from the group consisting of: a substituted or unsubstituted $C_{1-6}$ alkyl group, a substituted or unsubstituted $C_{1-6}$ alkoxy group,

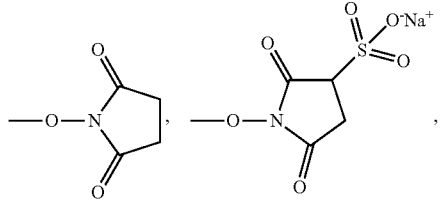

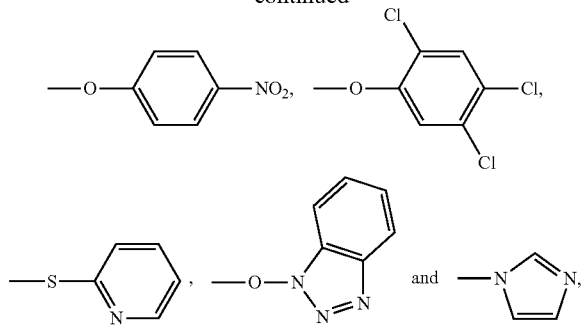

R₁ and R₂ are independently selected from the group consisting of: —H, a substituted or unsubstituted $C_{1-6}$ alkyl group, a substituted or unsubstituted $C_{1-6}$ alkoxy group, a substituted or unsubstituted $C_{3-6}$ cycloalkyl group and a substituted or unsubstituted $C_{4-10}$ alkylenecycloalkyl group, R₃ is selected from the group consisting of: —H, a substituted or unsubstituted $C_{1-6}$ alkyl group, a substituted or unsubstituted $C_{6-10}$ aralkyl group and a substituted or unsubstituted $C_{4-10}$ heterocyclic alkyl group;

the substituted group refers to a group which is substituted at one or more of available sites by one or more suitable groups, wherein the suitable group is selected from the group consisting of C1-6 alkyl, C1-6 alkoxy, C1-6 alkenyl, C1-6 alkynyl, C3-6 cycloalkyl, C6-12 aryl, phenoxyl, benzyl, C3-12 heterocyclic group which contains 1, 2 or 3 hetero atoms and wherein the hetero atom is/are one or more selected from the group consisting of N, O and S atoms, halogen, cyano, hydroxy, nitro, azide, C1-6 alkanoyl, primary amino, secondary amino, carboxyl, and ester;

after completion of the reaction, an acid anhydride is added to continue the reaction, and then separation and purification are carried out.

2. The preparation method according to claim 1, wherein the acid anhydride is an organic acid anhydride, and the organic acid anhydride is one or more selected from the group consisting of di-tert-butyl dicarbonate, acetic anhydride, propionic anhydride, isobutyric anhydride, butyric anhydride, benzoic anhydride and phthalic anhydride;

the molar ratio of the amount of the added acid anhydride to the reactant

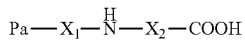

is from 0.01 to 10:1;

the reaction duration after the addition of the acid anhydride is 0.1 to 24 hours; or the step of the separation and purification comprises a step of separation and purification by ion exchange chromatography.

3. The preparation method according to claim 1, wherein the Y-branched hydrophilic polymer carboxylic acid derivative has a molecular weight of 15 to 50 KDa;

$P_a$ is a residue of one or more homopolymers selected from the group consisting of: polyethylene glycol, polypropylene glycol, polyvinyl alcohol, polytetrahydrofuran, polypropylene oxide, polybutyleneoxide, polyoxetane and polypropylene morpholine;

$P_a$ has a molecular weight of 7.5 to 25 KDa;

$P_b$ is a residue of one or more homopolymers selected from the group consisting of polyethylene glycol, polypropylene glycol, polyvinyl alcohol, polytetrahydrofuran, polypropylene oxide, polybutylene oxide, polyoxetane and polypropylene morpholine; and $P_b$ has a molecular weight of 7.5 to 25 KDa.

4. The preparation method according to claim 3, wherein $P_a$ is a polyethylene glycol residue having a structure of $R_a$—O—$(CH_2CH_2O)_m$—, wherein $R_a$ is selected from the group consisting of H, methyl, ethyl, isopropyl, cyclopropyl, cyclobutyl, cyclohexyl and benzyl, and m is an integer from 170 to 565; or $P_b$ is a polyethylene glycol residue having a structure of $R_b$—O—$(CH_2CH_2O)_n$—, wherein $R_b$ is selected from the group consisting of H, methyl, ethyl, isopropyl, cyclopropyl, cyclobutyl, cyclohexyl and benzyl, and n is an integer from 170 to 565.

5. The preparation method according to claim 3, wherein $R_a$ is H or a methyl group; $R_b$ is H or a methyl group; m and n are equal integers.

6. The preparation method according to claim 3, wherein the Y-branched hydrophilic polymer carboxylic acid derivative is a Y-branched polyethylene glycol carboxylic acid derivative, and the reaction is as follows:

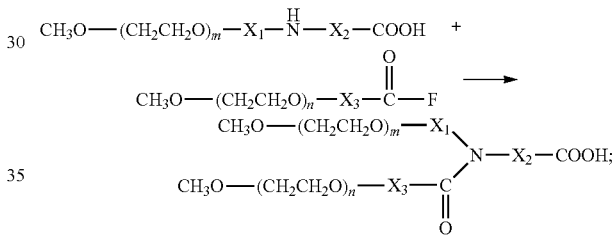

wherein m is an integer from 170 to 565, n is an integer from 170 to 565.

7. The preparation method according to claim 1, wherein $X_1$ and $X_3$ are independently selected from the group consisting of: a single bond, —$CH_2$—, —$CH_2CH_2$—, —$CH_2CH_2CH_2$—, —$CH_2CH_2CH_2CH_2$—, —$CH_2CH_2CH_2$ $CH_2CH_2$—, —$CH(CH_3)$—, —$CH_2CH(CH_3)$—, —$CH_2CH_2CH(CH_3)$—, —$CH_2CH_2CH_2CH(CH_3)$—, —$CH_2CH_2CH_2CH_2CH(CH_3)$—, —$CH_2CH_2CH_2CH_2$ $CH_2CH(CH_3)$—, —$(CH_2)_iO$— and —$(CH_2)_iCO$—, or the combination of two or more of these selections, i is an integer from 0 to 5;

$X_2$ is

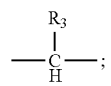

$R_3$ is selected from the group consisting of: —H, —$CH_3$, —$CH_2CH(CH_3)_2$, —$CH(CH_3)CH_2CH_3$, —$CH(CH_3)_2$,

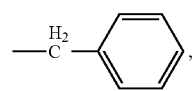

—CH₂OH, CH(OH)CH₃,
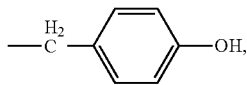
—CH₂COOH and —CH₂CH₂COOH; or
F is selected from the group consisting of: methoxy, ethoxy,
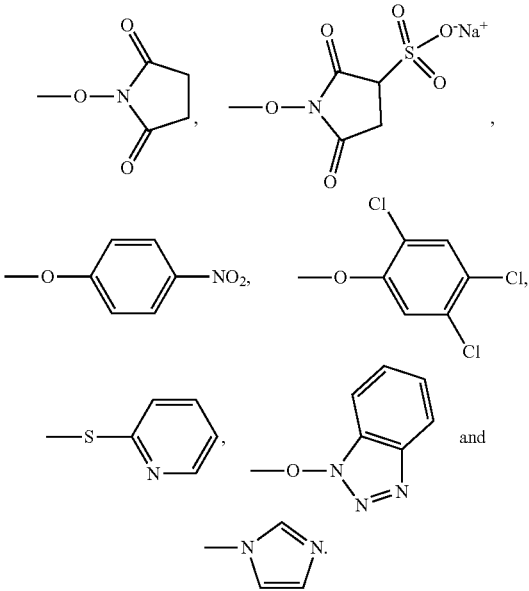
8. The preparation method according to claim 7, wherein $X_1$ is —CH₂CH₂—; $X_3$ is —CH₂—; $X_2$ is —CH₂— or —CH(CH₃)—; $R_3$ is H or —CH₃; and F is
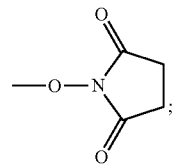
and the reaction in the preparation method is:
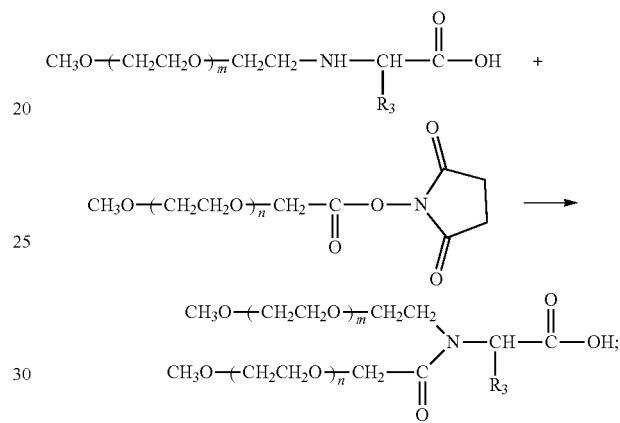
wherein m is an integer from 170 to 565, n is an integer from 170 to 565.
* * * * *